United States Patent
Retterath et al.

(10) Patent No.: US 9,671,328 B2
(45) Date of Patent: Jun. 6, 2017

(54) SYSTEM AND ASSESSMENT OF REFLECTIVE OBJECTS ALONG A ROADWAY

(71) Applicant: Facet Technology Corp., Eden Prairie, MN (US)

(72) Inventors: James E. Retterath, Excelsior, MN (US); Robert A. Laumeyer, Eden Prairie, MN (US)

(73) Assignee: Facet Technology Corp., Eden Prairie, MN (US)

( * ) Notice: Subject to any disclaimer, the term of this patent is extended or adjusted under 35 U.S.C. 154(b) by 0 days.

(21) Appl. No.: 15/148,722

(22) Filed: May 6, 2016

(65) Prior Publication Data
US 2016/0377529 A1    Dec. 29, 2016

Related U.S. Application Data

(60) Continuation of application No. 14/512,735, filed on Oct. 13, 2014, now Pat. No. 9,334,255, which is a
(Continued)

(51) Int. Cl.
*G01N 21/00*    (2006.01)
*G01N 21/25*    (2006.01)
(Continued)

(52) U.S. Cl.
CPC .......... *G01N 21/251* (2013.01); *G01N 21/55* (2013.01); *G01N 21/84* (2013.01); *G01S 17/06* (2013.01);
(Continued)

(58) Field of Classification Search
CPC ........ G02B 27/0172; G02B 2027/0178; G02B 2027/014; G02B 2027/0138;
(Continued)

(56) References Cited

U.S. PATENT DOCUMENTS 3,636,250 A    1/1972  Haeff
4,348,652 A    9/1982  Barnes et al.
(Continued)

OTHER PUBLICATIONS

Dominant Color Transform and Circular Pattern Vector for Traffic Sign Detection and Recognition, Jung Hak and Tae Young Choi, IEICE Transaction Fundamentals, vol. E81-A, No. 6, pp. 1128-1135, Jun. 1998.
(Continued)

*Primary Examiner* — Michael P Stafira
(74) *Attorney, Agent, or Firm* — Patterson Thuente Pedersen, P.A.

(57) ABSTRACT

A system for classifying different types of sheeting materials of road signs depicted in a videostream compares estimated retroreflectivity values against known minimum retroreflectivity values for each of a plurality of colors. Once a road sign has been identified in the videostream, the frames associated with that road sign are analyzed to determine each of a plurality of colors present on the road sign. An estimated retroreflectivity for each of the plurality of colors present on the road sign is then determined. By comparing the estimated retroreflectivity for each of the plurality of colors against known minimum retroreflectivity values for the corresponding color for different types of sheeting materials, an accurate determination of the classification of the sheeting material of the road sign is established. Preferably, certain conditions of gross failure of the sheeting material are filtered out before classification of the sheeting material is determined.

22 Claims, 18 Drawing Sheets

Related U.S. Application Data continuation of application No. 14/025,614, filed on Sep. 12, 2013, now Pat. No. 8,860,944, which is a division of application No. 13/205,337, filed on Aug. 8, 2011, now Pat. No. 8,660,311, which is a division of application No. 12/419,843, filed on Apr. 7, 2009, now Pat. No. 7,995,796, which is a continuation of application No. 11/056,926, filed on Feb. 11, 2005, now Pat. No. 7,515,736, which is a continuation of application No. 09/928,218, filed on Aug. 10, 2001, now Pat. No. 6,891,960.

(60) Provisional application No. 60/224,761, filed on Aug. 12, 2000, provisional application No. 60/296,596, filed on Jun. 7, 2001.

(51) Int. Cl.
| | | |
|---|---|---|
| *G08G 1/0967* | (2006.01) | |
| *G01N 21/55* | (2014.01) | |
| *G01N 21/84* | (2006.01) | |
| *G01S 17/06* | (2006.01) | |
| *G06K 9/00* | (2006.01) | |
| *G06K 9/20* | (2006.01) | |
| *G06K 9/46* | (2006.01) | |

(52) U.S. Cl.
CPC ....... *G06K 9/00818* (2013.01); *G06K 9/2036* (2013.01); *G06K 9/4652* (2013.01); *G06K 9/4661* (2013.01); *G08G 1/096758* (2013.01); *G08G 1/096783* (2013.01); *G01N 2201/06113* (2013.01); *G01N 2201/102* (2013.01); *G01N 2201/12* (2013.01)

(58) Field of Classification Search
CPC .......... G02B 2027/0187; G02B 27/017; G02B 2027/0132; G02B 26/0808; G02B 26/0816; G02B 2027/0174; G02B 27/0093; G02B 27/225; G02B 6/005
See application file for complete search history.

(56) References Cited

U.S. PATENT DOCUMENTS

| | | |
|---|---|---|
| 4,373,819 A | 2/1983 | Pallotta |
| 4,491,923 A | 1/1985 | Look |
| 4,721,389 A | 1/1988 | Dejaiffe |
| 4,726,134 A | 2/1988 | Woltman |
| 4,920,385 A | 4/1990 | Clarke et al. |
| 5,050,327 A | 9/1991 | Woltman |
| 5,051,906 A | 9/1991 | Evans et al. |
| 5,164,785 A | 11/1992 | Hopkins et al. |
| 5,373,357 A | 12/1994 | Hopkins et al. |
| 5,392,365 A | 2/1995 | Steinkirchner |
| 5,448,484 A | 9/1995 | Bullock et al. |
| 5,465,115 A | 11/1995 | Conrad et al. |
| 5,465,308 A | 11/1995 | Hutcheson et al. |
| 5,530,549 A | 6/1996 | Brown |
| 5,533,388 A | 7/1996 | Yamamoto et al. |
| 5,579,471 A | 11/1996 | Barber et al. |
| 5,627,915 A | 5/1997 | Rosser et al. |
| 5,633,944 A | 5/1997 | Guibert et al. |
| 5,633,946 A | 5/1997 | Lachinski et al. |
| 5,643,476 A | 7/1997 | Garmire et al. |
| 5,647,058 A | 7/1997 | Agrawal et al. |
| 5,696,503 A | 12/1997 | Nasburg |
| 5,699,444 A | 12/1997 | Palm |
| 5,740,274 A | 4/1998 | Ono et al. |
| 5,757,878 A | 5/1998 | Dobbs et al. |
| 5,764,411 A | 6/1998 | Shanks |
| 5,790,691 A | 8/1998 | Narayanswamy et al. |
| 5,793,034 A | 8/1998 | Wesolowicz et al. |
| 5,802,361 A | 9/1998 | Wang et al. |
| 5,812,267 A | 9/1998 | Everett, Jr. et al. |
| 5,818,640 A | 10/1998 | Watanabe et al. |
| 5,844,699 A | 12/1998 | Usami et al. |
| 5,852,823 A | 12/1998 | De Bonet |
| 5,864,630 A | 1/1999 | Cosatto et al. |
| 5,892,847 A | 4/1999 | Johnson |
| 5,893,095 A | 4/1999 | Jain et al. |
| 5,911,139 A | 6/1999 | Jain et al. |
| 5,915,032 A | 6/1999 | Look |
| 5,938,319 A | 8/1999 | Hege |
| 5,941,944 A | 8/1999 | Messerly |
| 5,949,914 A | 9/1999 | Yuen |
| 5,950,190 A | 9/1999 | Yeager et al. |
| 5,974,521 A | 10/1999 | Akerib |
| 5,983,237 A | 11/1999 | Jain et al. |
| 5,991,085 A | 11/1999 | Rallison |
| 6,011,515 A | 1/2000 | Radcliffe et al. |
| 6,018,697 A | 1/2000 | Morimoto et al. |
| 6,023,967 A | 2/2000 | Chung et al. |
| 6,036,322 A | 3/2000 | Nilsen et al. |
| 6,048,069 A | 4/2000 | Nagaoka et al. |
| 6,064,768 A | 5/2000 | Hajj et al. |
| 6,084,595 A | 7/2000 | Bach et al. |
| 6,123,263 A | 9/2000 | Feng |
| 6,134,819 A | 10/2000 | McClain et al. |
| 6,141,433 A | 10/2000 | Moed et al. |
| 6,141,434 A | 10/2000 | Christian et al. |
| 6,142,871 A | 11/2000 | Inoue |
| 6,166,813 A | 12/2000 | Roberts |
| 6,173,231 B1 | 1/2001 | Chojnacki |
| 6,208,386 B1 | 3/2001 | Wilf et al. |
| 6,212,480 B1 | 4/2001 | Dunne |
| 6,226,636 B1 | 5/2001 | Abdel-Mottaleb et al. |
| 6,240,424 B1 | 5/2001 | Hirata |
| 6,240,664 B1 | 6/2001 | Hjaltason |
| 6,253,477 B1 | 7/2001 | Balint |
| 6,266,442 B1 | 7/2001 | Laumeyer et al. |
| 6,271,840 B1 | 8/2001 | Finseth et al. |
| 6,292,227 B1 | 9/2001 | Wilf et al. |
| 6,363,161 B2 | 3/2002 | Laumeyer et al. |
| 6,382,126 B1 | 5/2002 | Findley |
| 6,389,417 B1 | 5/2002 | Shin et al. |
| 6,389,424 B1 | 5/2002 | Kim et al. |
| 6,405,132 B1 | 6/2002 | Breed et al. |
| 6,407,674 B1 | 6/2002 | Gallagher |
| 6,411,953 B1 | 6/2002 | Ganapathy et al. |
| 6,424,914 B1 | 7/2002 | Lin |
| 6,438,130 B1 | 8/2002 | Kagan et al. |
| 6,449,384 B2 | 9/2002 | Laumeyer et al. |
| 6,453,056 B2 | 9/2002 | Laumeyer et al. |
| 6,463,432 B1 | 10/2002 | Murakawa |
| 6,476,910 B1 | 11/2002 | Hermes |
| 6,502,105 B1 | 12/2002 | Yan et al. |
| 6,507,441 B1 | 1/2003 | Eisenberg et al. |
| 6,514,597 B1 | 2/2003 | Strobel et al. |
| 6,526,352 B1 | 2/2003 | Breed et al. |
| 6,538,751 B2 | 3/2003 | Ono |
| 6,558,021 B2 | 5/2003 | Wu et al. |
| 6,563,959 B1 | 5/2003 | Troyanker |
| 6,566,710 B1 | 5/2003 | Strachan et al. |
| 6,567,103 B1 | 5/2003 | Chaudhry |
| 6,567,551 B2 | 5/2003 | Shiiyama |
| 6,574,378 B1 | 6/2003 | Lim |
| 6,574,616 B1 | 6/2003 | Saghir |
| 6,575,378 B2 | 6/2003 | Aoki et al. |
| 6,584,221 B1 | 6/2003 | Moghaddam et al. |
| 6,594,931 B1 | 7/2003 | Barton et al. |
| 6,611,628 B1 | 8/2003 | Sekiguchi et al. |
| 6,625,315 B2 | 9/2003 | Laumeyer et al. |
| 6,653,990 B1 | 11/2003 | Lestruhaut |
| 6,674,878 B2 | 1/2004 | Retterath et al. |
| 6,711,280 B2 * | 3/2004 | Stafsudd ............ G06K 9/3241 348/622 |
| 6,772,062 B2 | 8/2004 | Lasky et al. |
| 6,778,697 B1 | 8/2004 | Shin et al. |
| 6,885,767 B1 | 4/2005 | Howell |
| 6,888,622 B2 | 5/2005 | Shimomura |
| 6,891,960 B2 | 5/2005 | Retterath et al. |
| 7,043,057 B2 | 5/2006 | Retterath et al. |

(56) References Cited

U.S. PATENT DOCUMENTS

| | | |
|---|---|---|
| 7,082,426 B2 | 7/2006 | Musgrove et al. |
| 7,092,548 B2 | 8/2006 | Laumeyer et al. |
| 7,173,707 B2 | 2/2007 | Retterath et al. |
| 7,409,110 B2 | 8/2008 | Kayahara |
| 7,411,681 B2 | 8/2008 | Retterath et al. |
| 7,440,003 B2 | 10/2008 | Shimamura et al. |
| 7,444,003 B2 | 10/2008 | Laumeyer et al. |
| 7,515,736 B2 | 4/2009 | Retterath et al. |
| 7,590,310 B2 | 9/2009 | Retterath et al. |
| 7,995,796 B2 | 8/2011 | Retterath et al. |
| 8,150,216 B2 | 4/2012 | Retterath et al. |
| 8,660,311 B2 | 2/2014 | Retterath et al. |
| 8,860,944 B2 | 10/2014 | Retterath et al. |
| 9,335,255 B2 | 5/2016 | Retterath et al. |
| 2001/0021011 A1 | 9/2001 | Ono |
| 2001/0036293 A1 | 11/2001 | Laumeyer et al. |
| 2001/0043717 A1 | 11/2001 | Laumeyer et al. |
| 2001/0043718 A1 | 11/2001 | Laumeyer et al. |
| 2001/0045034 A1 | 11/2001 | Mueller et al. |
| 2002/0044278 A1 | 4/2002 | Le |
| 2002/0063638 A1 | 5/2002 | Gallagher |
| 2002/0090492 A1 | 7/2002 | Haunschild et al. |
| 2002/0106109 A1 | 8/2002 | Retterath et al. |
| 2002/0163942 A1 | 11/2002 | Baillargeon et al. |
| 2002/0186865 A1 | 12/2002 | Retterath et al. |
| 2003/0016869 A1 | 1/2003 | Laumeyer et al. |
| 2003/0090415 A1 | 5/2003 | Miyasaka et al. |
| 2003/0174054 A1 | 9/2003 | Shimomura |
| 2004/0062442 A1 | 4/2004 | Laumeyer et al. |
| 2004/0127614 A1 | 7/2004 | Jiang et al. |
| 2004/0156531 A1 | 8/2004 | Retterath et al. |
| 2004/0218910 A1 | 11/2004 | Chang et al. |
| 2005/0021472 A1 | 1/2005 | Gettman et al. |
| 2005/0249378 A1 | 11/2005 | Retterath et al. |
| 2005/0271304 A1 | 12/2005 | Retterath et al. |
| 2006/0262312 A1 | 11/2006 | Retterath et al. |
| 2007/0043707 A1 | 2/2007 | Kulkarni et al. |
| 2007/0081744 A1 | 4/2007 | Gokturk et al. |
| 2007/0154067 A1 | 7/2007 | Laumeyer et al. |
| 2007/0216904 A1 | 9/2007 | Retterath et al. |
| 2009/0252376 A1 | 10/2009 | Retterath et al. |
| 2010/0082597 A1 | 4/2010 | Retterath et al. |
| 2012/0065940 A1* | 3/2012 | Retterath ......... G08G 1/096758 702/189 |
| 2013/0271613 A1 | 10/2013 | Retterath et al. |
| 2014/0036269 A1 | 2/2014 | Retterath et al. |
| 2015/0153271 A1 | 6/2015 | Retterath et al. |

OTHER PUBLICATIONS

A Trainable Pedestrian Detection System, C. Papageorgiou, T. Evgenious, T. Poggio, Center for Biological And Computational Learning and Artificial Intelligence Laboratory, MIT, IEEE International Conference on Intelligent Vehicles, pp. 241-246, 1998.
Robust Lane Recognition Embedded in a Real-Time Driver Assistance System, R. Risack, P. Klausmann, W. Kruger, W. Enkelmann, Fraunhofer-Institut fur Informations, Karlsruhe, Germany, IEEE International Conference on Intelligent Vehicles, pp. 35-40, 1998.
A Texture-based Object Detection and an Adaptive Model-based Classification, T. Kalinke, C. Tzomakas, W. Seelen, Institut fur Neuroinformatik, Bochum, Germany, IEEE International Conference on Intelligent Vehicles, pp. 143-148, 1998.
Internet Printout: The Road Sign Recognition System—RS[2], Faculty of Transportation Sciences, Prague, Czech Republic, 7 pgs., c. approximately 1999.
Internet Printout: The Chamfer System, 4 pgs., c. approximately 1999.
Real-Time Object Recognition: Hierarchical Image Matching in a Parallel Virtual Machine Environment, J. You, P. Bhattacharya, S. Hungenahally, School of Computing and Information Technology, Griffith University, Brisbane, Australia, Dept. of Computer Engineering, University of Nebraska, Lincoln, Nebraska, 3 pgs., undated. (1994).
An Architecture of Object Recognition System for Various Images Based on Multi-Agent, Keiji Yanai, Koichiro Deguchi, Dept. of Computer Science, University of Electro-Communications, Tokyo, Japan, and Dept. of Mathematical Engineering and Information Physics, University of Tokyo, Tokyo, Japan, 4 pgs., undated. (1998).
Multi-Feature Matching Algorithm for Free-Form 3D Surface Registration, C. Schutz, T. Jost, H, Hugli, Institute for Microtechnology, Neuchatel, Switzerland, 3 pgs., undated. (Aug. 1998).
Representation of Uncertainty in Spatial Target Tracking, Tim Baker, Malcolm Strens, DERA Farnborough, United Kingdom, 4 pgs., undated. (1998).
Using Centroid Covariance in Target Recognition, Gang Liu and Robert M. Haralick, Dept. of Electrical Engineering, University ofWashington, Seattle, Washington, 4 pgs., undated. (1998).
Using Spatial Sorting and Ranking in Model Based Object Recognition, G. Hjaltason, M. Ray, H. Samet, I. Weiss, Computer Science Dept. University of Maryland, College Park, Maryland, 3 pgs., undated. (Aug 1998).
Surveillance Systems for Terrestrial Transport Safety and Improved User Information Capability, C. Nwagboso, C. Regazzoni, M. Renard, E. Stringa, Bolton Institute, Bolton, United Kingdom, Dept. of Biophysical & Electronic Engineering, Genova, Italy, Vigitec, Brussels, Belgium, pp. 1-7, undated. (1998).
Landmark Recognition using Projection Learning for Mobile Robot Navigation, Ren C. Luo, Harsh Potlapalli, Center for Robotics and Intelligent Machines, IEEE World Congress on Computational Intelligence, vol. IV, pp. 2703-2708, Jun. 1994.
A Real-Time Traffic Sign Recognition System, S. Estable, J. Schick, F. Stein, R.Janssen, R. Ott, W. Ritter, Y.-J. Zheng, Daimler-Benz Research Center, Proceedings of the Intelligent Vehicles '94 Symposium, Paris, France, pp. 213- 218, Oct. 1994.
Recognition of Traffic Signs by Artificial Neural Network, D. Ghica, S. Lu, X.Yuan, Dept. of Computer Science Memorial University of Newfoundland, IEEE, pp. 1444-1449, Mar. 1995.
Realtime Traffic Sign Recognition (TSR), Jens Logemann, Ed., Univeritat Koblenz-Landau, 3 pgs., Nov. 1997.
Registering Multiple Cartographic Models with the Hierarchical Mixture of Experts Algorithm, Simon Moss and Edwin R. Hancock, Dept. Of Computer Science, University of New York, IEEE, pp. 909-914, 1997.
Multi-Modal Tracking of Faces for Video Communications, James L. Crowley and Francois Berard, GRAVIR—IMAG, I.N.P. Grenoble, Grenoble, France, IEEE, pp. 640-645, 1997.
Road Traffic Sign Detection and Classification, A. Escalera, L. Moreno, M. Salichs, J. Armingol, IEEE Transactions on Industrial Electronics, vol. 44, No. 6, pp. 848-859, Dec. 1997.
Mandal, "Illumination Invariant Image Indexing Using Moments and Wavelets" Journal of Electronic Imaging, Apr. 1998 pp. 282-293, vol. 7 (2), USA.
Celentano, "Feature Integration and Relevance Feedback Analysis in Image.Similarity Evaluation" Journal of Electronic Imaging, Apr. 1998, pp. 308-317 vol. 7(2), USA.
Estevez, Auto-Associatve Segmentation for Real-Time Object Recognition in Realistic Outdoor Images, Journal of Electronic Imaging, Apr. 1998 pp. 378- 385 vol. 7(2), USA.
J Patrick Bixler, Department of Computer Science, Virginia Tech, Blacksburg, Virginia; David P. Miller Artificial Intelligence Group, Jet Propulsion Laboratory, California Institute of Technology, Pasadena, California, "Extracting text from real-world scenes", Article, 8 pp., 1988.
Carson et al., "Region Base Image Querying," Proc. Of IEEE CUPR Workshop on Content-Based Access of Images and Video Libraries, 1997.
Lui et al., "Scalable Object-Based Image Retrieval," a pdf paper, Sep. 2003.
Ozer et al., "A Graph Based Object Description for Information Retrieval in Digital Image and Video Libraries," a pdf paper, 1998.
Fan et al., "Automatic Model-Based Semantic Object Extraction Algorithm," IEEE Trans on Circuits and Systems for Video Technology, vol. 11, No. 10, Oct. 2001, pp. 1073.
Ardizzoni et al., "Windsurf: Region Based Image Retrieval Using Wavelets," Proc. Of the 1st Int'l Workshop on Similarity Search, Sep. 1999, pp. 167-173.

(56) References Cited

OTHER PUBLICATIONS

Maerz et al., Surveyor: Mobile Highway Inventory and Measurement System [on-line], [retrieved on Dec. 12, 2012]. Retrieved from the internet: http://web.mst.edu/~norbert/ref.htm, dated 1999, pp. 135-142.

McGee et al., An Implementation Guide for Minimum Retroreflectivity Requirements for Traffic Signs [on-line], Apr. 1998 [retrieved on Apr. 26, 2013], U.S. Department of Commerce National Technical Information Service, Publication No. FHWA-RD-97-052, 60 pages. Retrieved from the Internet: http://trid.trb.org/view/aspx?id=483855.

Hyaltason et al., Using Spatial Sorting and Ranking in Model-Based Object Recognition [on-line], Aug. 16-20, 1998 [retrieved on Oct. 1, 2013], Fourteenth International Conference on Pattern Recognition, 1998, vol. 2, pp. 1347-1349. Retrieved from the Internet: http://ieeexplore.ieee.org/xpls/abs_all.jsp?amumber=711951.

Janssen et al., Hybrid Approach for Traffic Sign Recognition [on-line], Jul. 14-16, 1993 [retrieved on Oct. 1, 2013], Intelligent Vehicles '93 Symposium, pp. 390-395. Retrieved from the Internet: http://ieeexplore.ieee.org/xpls/abs_all.jsp?amumber=697358.

Application and File History for U.S. Appl. No. 11/122,969, filed May 5, 2005, now U.S. Pat. No. 7,590,310, Inventors Retterath et al.

Application and File History for U.S. Appl. No. 09/177,836, filed Oct. 23, 1998, now U.S. Pat. No. 6,266,442, Inventors Laumeyer et al.

Application and File History for U.S. Appl. No. 09/772,191, filed Jan. 29, 2001, now U.S. Pat. No. 6,449,384, Inventors Laumeyer et al.

Application and File History for U.S. Appl. No. 09/812,753, filed Mar. 20, 2001, now U.S. Pat. No. 6,453,056, Inventors Laumeyer et al.

Application and File History for U.S. Appl. No. 09/883,816, filed Jun. 18, 2001, now U.S. Pat. No. 6,363,161, Inventors Laumeyer et al.

Application and File History for U.S. Appl. No. 10/244,318, filed Sep. 16, 2002, now U.S. Pat. No. 6,625,315, Inventors Laumeyer et al.

Application and File History for U.S. Appl. No. 10/634,630, filed Aug. 5, 2003, now U.S. Pat. No. 7,092,548, Inventors Laumeyer et al.

Application and File History for U.S. Appl. No. 11/457,255, filed Jul. 13, 2006, now U.S. Pat. No. 7,444,003, Inventors Laumeyer et al.

Application and File History for U.S. Appl. No. 09/928,218, filed Aug. 10, 2001, now U.S. Pat. No. 6,891,960, Inventors Retterath et al.

Feb. 11, 2005, now U.S. Pat. No. 7,515,736, Inventors Retterath et al.

Application and File History for U.S. Appl. No. 12/419,843, filed. Apr. 7, 2009, now U.S. Pat. No. 7,995,796, Inventors Retterath et al.

Application and File History for U.S. Appl. No. 09/918,375, filed Jul. 30, 2001, now U.S. Pat. No. 6,674,878, Inventors Retterath et al.

Application and File History for U.S. Appl. No. 10/736,454, filed Dec. 15, 2003, now U.S. Pat. No. 7,043,057, Inventors Retterath et al.

Application and File History for U.S. Appl. No. 11/381,503, filed May 3, 2006, now U.S. Pat. No. 7,173,707, Inventors Retterath et al.

Application and File History for U.S. Appl. No. 11/702,421, filed Feb. 5, 2007, now U.S. Pat. No. 7,411,681, Inventors Retterath et al.

Application and File History for U.S. Appl. No. 12/584,894, filed Sep. 14, 2009, now U.S. Pat. No. 8,150,216, Inventors Retterath et al.

Application and File History for U.S. Appl. No. 13/781,017, filed Feb. 28, 2013, Inventors Retterath et al.

Application and File History for U.S. Appl. No. 13/205,337, filed Aug. 8, 2011, now U.S. Pat. No. 8,660,311. Inventors Retterath et al.

Application and File History for U.S. Appl. No. 14/025,614, filed Sep. 12, 2013, now U.S. Pat. No. 8,860,944. Inventors Retterath et al.

Application and File History for U.S. Appl. No. 14/512,735, filed Oct. 13, 2014, now U.S. Pat. No. 9,335,255. Inventors Retterath et al.

Long, Michigan DOT Reflects on Signs, Oct. 1997 [retrieved Jan. 11, 2017], Transportation Research Board, Issue 192, pp. 24-25. Retrieved from the Internet: https://trid.trb.org/view.aspx?id=474202.

Lumia, A mobile system for measuring retroreflectance of traffic signs, Mar. 1, 1991 [retrieved Jan. 11, 2017], Proc. SPIE, Optics, Illumination, and Image Sensing for Machine Vision V, vol. 1385, pp. 15-26. Retrieved from the Internet: http://proceedings.spiedigitallibrary.org/proceeding.aspx?articleid=954038.

\* cited by examiner

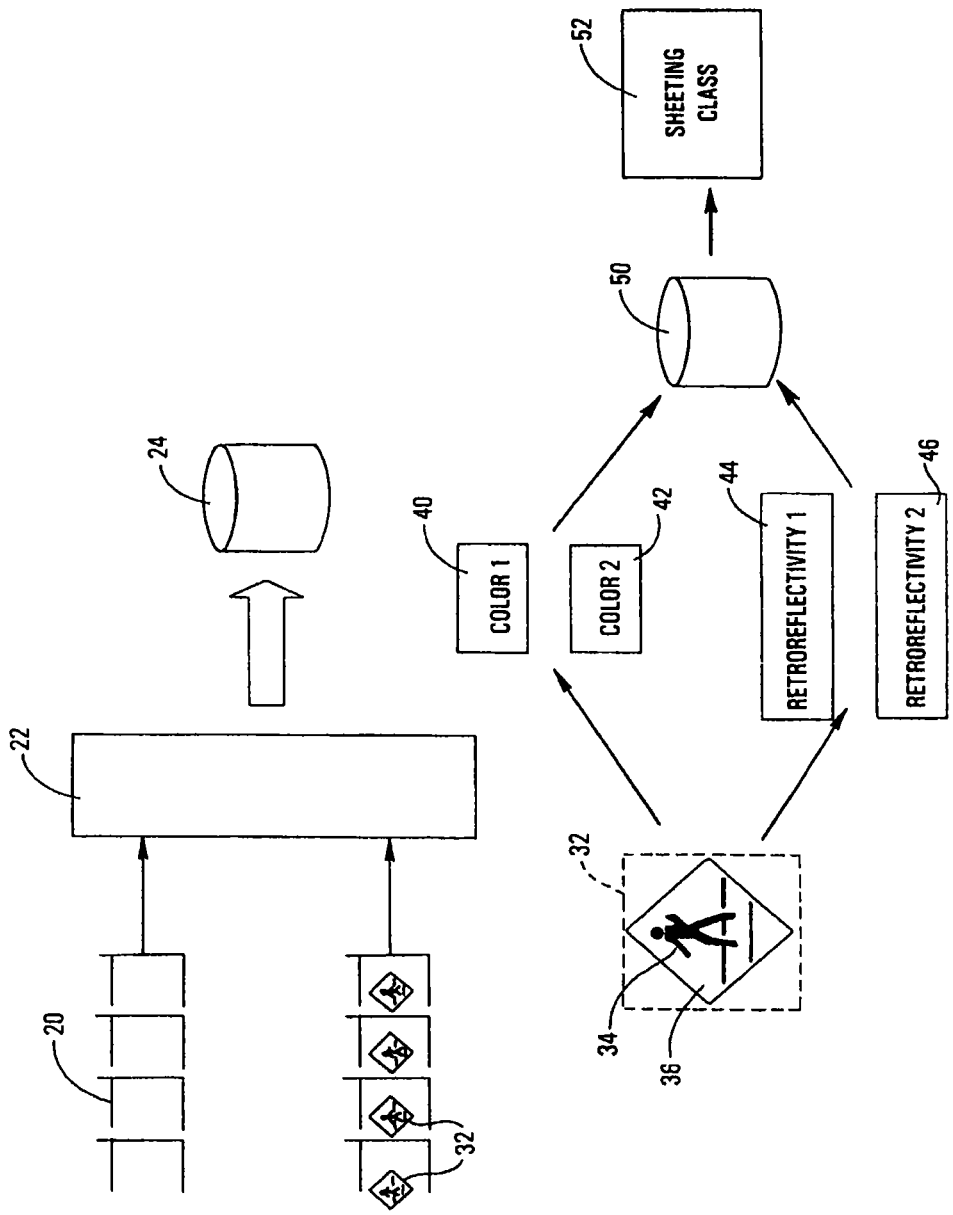

*Fig.14A*          *Fig.14B*
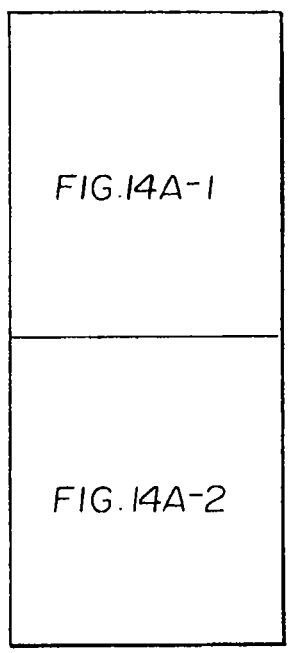 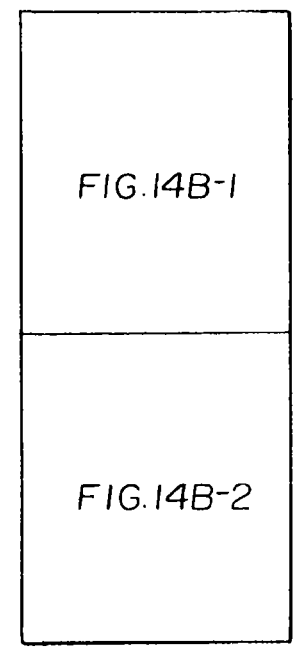

SYSTEM AND ASSESSMENT OF REFLECTIVE OBJECTS ALONG A ROADWAY

RELATED APPLICATIONS

The present application is a continuation of U.S. application Ser. No. 14/512,735, filed Oct. 13, 2014, now U.S. Pat. No. 9,335,255, which is a continuation of U.S. application Ser. No. 14/025,614, filed Sep. 12, 2013, now U.S. Pat. No. 8,860,944, which is a divisional of U.S. application Ser. No. 13/205,337, filed Aug. 8, 2011, now U.S. Pat. No. 8,660,311, which is a divisional of U.S. application Ser. No. 12/419,843, filed Apr. 7, 2009, now U.S. Pat. No. 7,995,796, which is a continuation of application Ser. No. 11/056,926, filed Feb. 11, 2005, now U.S. Pat. No. 7,515,736, which is a continuation of application Ser. No. 09/928,218, filed Aug. 10, 2001, now U.S. Pat. No. 6,891,960, which claims the benefit of the contents and filing date accorded to two U.S. Provisional patent applications, the first of which was filed on Aug. 12, 2000 as Application No. 60/224,761, and the second of which was filed on Jun. 7, 2001 as Application No. 60/296,596. The application is related to U.S. Pat. No. 6,674,878, issued Jan. 6, 2004, and U.S. Pat. No. 6,453,056, issued Sep. 17, 2002, which is a continuation of U.S. Pat. No. 6,266,442, filed Oct. 23, 1998, all of which are hereby incorporated by reference.

FIELD OF THE INVENTION

The present invention relates generally to the field of automated object recognition. More specifically, the present invention relates to a system for classifying different types of sheeting materials of road signs depicted in a videostream.

BACKGROUND OF THE INVENTION

The goal of using an automated image identification system to recognize road signs and traffic signs is well known. Various techniques have been proposed for the recognition of road signs as part of a real-time automated vehicle navigation system. Due to the processing limitations imposed by a real-time environment, almost all of these techniques have involved template matching of shape and color. Given the wide variations in lighting and conditions, few if any of these systems provide accurate results.

Another use of automated road sign recognition is for the purpose of identifying and creating an accurate inventory of all road signs and traffic signs along a given street or highway. In one system as described in U.S. Pat. No. 6,266,442, entitled, "METHOD AND APPARATUS FOR IDENTIFYING OBJECTS DEPICTED IN A VIDEOSTREAM," issued Jul. 24, 2001 to Laumeyer et al., an acquisition vehicle equipped with video cameras and position identifying technology, such as global positioning satellite (GPS) receivers, is systematically driven over the roads and streets in a given area to produce a videostream tagged with location information. The tagged videostream is analyzed by computer software routines to perform object recognition of the desired objects, the road signs in this case. The results of this analysis are exported to an asset management database that stores attributes of the road signs.

Road signs are manufactured from a sheeting material made up of multiple layered films (one or more colored layers that are fused with a layer that produces the reflectivity) that is adhered to the sign face. There are different types of sheeting material utilized in the road sign industry. Currently, specific attributes about each road sign like retroreflectivity (measured in candelas/lux/sq. meter) and sheeting type must be gathered manually by sending personnel in the field to measure retroreflectivity with a handheld device (like the Impulse RM retro-reflectometer from Laser Technology, Inc.) and to visually determine the sheeting type of each sign. Measurements of retroreflectivity and identification of sheeting type are helpful in evaluating the visibility of a sign and whether it has deteriorated due to a breakdown in the pigments or reflective material in the sheeting material of the sign. The retroreflectivity and sheeting type can also be used to produce a predictive model of how the sign will perform into the future based on the as-measured characteristics.

Generally, highway and street maintenance departments do not systematically evaluate the deterioration of the reflective materials used on road signs and markers. If inspections of road signs or markers are performed, they are typically accomplished by having inspectors manually position a handheld retroreflectometer directly on the surface of a sign in order to determine a retroreflectivity value for that sign. When there are a large number of road signs or markers (sometimes referred to as traffic control devices or TCDs) in a given jurisdiction, the task of manually inspecting all of these road signs and markers can be time consuming and expensive.

One technique for determining retroreflectivity, designated as "$R_A$" generally (and from time to time in this disclosure), which does not require that a retroreflectometer be placed directly on a sign is described in U.S. Pat. No. 6,212,480 entitled, "APPARATUS AND METHOD FOR DETERMINING PRECISION REFLECTIVITY OF HIGHWAY SIGNS AND OTHER REFLECTIVE OBJECTS UTILIZING AN OPTICAL RANGE FINDER INSTRUMENT" issued Apr. 3, 2001 to Dunne. The Dunne patent relates to a device commercialized by the assignee thereof and marketed as the "Impulse RM" retro-reflectometer by Laser Technology, Inc., of Englewood, Colo., USA. In use, handheld devices fabricated according to the Dunne patent are manually directed toward, or precisely at, a target object and then manually "fired." Once fired, the handheld device bounces a laser off the target object and measures the reflected laser energy that is then used to determine a retroreflectivity.

There are several drawbacks of the handheld laser arrangement described by the Dunne patent. The handheld device can only measure a single color at a time and can only measure one object at a time. The determination of retroreflectivity for a given object is valid only for the actual location, or discrete measurement point, along the roadway at which the measurement was made by the human operator. In order to validate a measurement made by such devices, the device must be taken back to the precise location in the field where an original measurement occurred for a valid comparison measurement to be made.

Another technique established for determining the retroreflectivity of signs has been introduced by the Federal Highway Administration (FHWA). The Sign Management and Retroreflectivity Tracking System (SMARTS) is a vehicle that contains one high intensity flash source (similar to the Honeywell StrobeGuard™ SG-60 device), one color camera, two black and white cameras, and a range-sensing device. The SMARTS vehicle requires two people for proper operation—one driver and one system operator to point the device at the target sign and arm the system. The SMARTS travels down the road, and the system operator "locks on" to a sign up ahead by rotating the camera and light assembly to point at the sign. At a distance of 60 meters, the system triggers the flash source to illuminate the sign surface, an image of which is captured by one of the black and white cameras. A histogram is produced of the sign's legend and background that is then used to calculate retroreflectivity. A GPS system stores the location of the vehicle along with the calculated retroreflectivity in a computer database.

Like the handheld laser device of the Dunne patent, the SMARTS device can only determine retroreflectivity for one sign at a time and can only determine retroreflectivity for the discrete point on the roadway 60 meters from the sign. Two people are required to operate the vehicle and measurement system. The SMARTS vehicle cannot make retroreflectivity determinations for signs on both sides of the roadway in a single pass over the roadway, and does not produce nighttime sign visibility information for lanes on the roadway not traveled by the vehicle. Because the system operator in the SMARTS vehicle must locate and track signs to be measured while the vehicle is in motion, a high level of operational skill is required and the likelihood that a sign will be missed is significant. Most importantly for purposes of the present invention, the SMARTS device makes no attempt to automatically determine sheeting type of a sign.

There are an estimated 58 million individual TCDs that must be monitored and maintained in the United States and new TCD installations increase this number daily. For the reasons that have been described, the existing techniques for determining retroreflectivity do not lend themselves to increasing processing throughput so as to more easily manage the monitoring and maintenance of these TCDs. So called automated data collection systems often require that normal traffic be stopped during data collection because either the acquisition vehicle moved very slowly or because the acquisition vehicle had to come to a full stop before recording data about the roadside scene. Furthermore, a human operator is required to point one or more measurement devices at a sign of interest, perform data collection for that particular sign and then set up the device for another particular sign of interest. With such a large number of TCDs that must be monitored, it would be desirable to provide an automated system for determining the retroreflectivity of road signs and markers that addresses these and other shortcomings of the existing techniques to enable a higher processing throughput of an automated determination of the retroreflectivity and sheeting classification of road signs and markers.

SUMMARY OF THE INVENTION

The present invention is a system for classifying different types of sheeting materials of road signs depicted in a videostream. Once a road sign has been identified in the videostream, the frames associated with that road sign are analyzed to determine each of a plurality of colors present on the road sign. An estimated retroreflectivity for each of the plurality of colors present on the road sign is then determined. By comparing the estimated retroreflectivity for each of the plurality of colors against known minimum retroreflectivity values for the corresponding color for different types of sheeting materials, an accurate determination of the classification of the sheeting material of the road sign is established. Preferably, certain conditions of gross failure of the sheeting material are filtered out before classification of the sheeting material is determined.

In a preferred embodiment, a system for the automated determination of retroreflectivity values for reflective surfaces disposed along a roadway is utilized to establish the retroreflectivity values for both foreground and background colors of a road sign for the purpose of classifying the sheeting material of that sign. An area along the roadway that includes at least one reflective surface is repeatedly illuminated by a light source and multiple light intensity values are measured over a field of view which includes at least a portion of the area illuminated by the light source. A computer processing system is used to identify a portion of the light intensity values associated with a reflective surface and analyze the portion of the light intensity values to determine at least one retroreflectivity value for that reflective surface. Color images of the area and locational information are also generated by the system and are used together with a characterization profile of the light source to enhance the accuracy of the determination of retroreflectivity values.

In contrast to the existing techniques for determining retroreflectivity that require an operator to target individual signs from a known distance, a preferred embodiment of the present invention can determine retroreflectivity without targeting individual signs and can automatically determine sheeting classification as a result. To overcome the limitations imposed by the existing techniques, the preferred embodiment employs several enhancements that are designed to improve the accuracy of evaluating intensity measurements made over a view where the reflective surfaces are not individually targeted and therefore neither the distance to the reflective surface or the normal vector to the reflective surface are known.

BRIEF DESCRIPTION OF THE DRAWINGS

FIG. 2 is a data flow diagram of a preferred embodiment of the present invention.

FIGS. 14A, 14A-1, 14A-2 and 14B, 14B-1, 14B-2 depict a flowchart for a preferred embodiment of the threshold algorithm used to determine sign sheeting type.

DETAILED DESCRIPTION OF THE PREFERRED EMBODIMENTS

Figure 1:
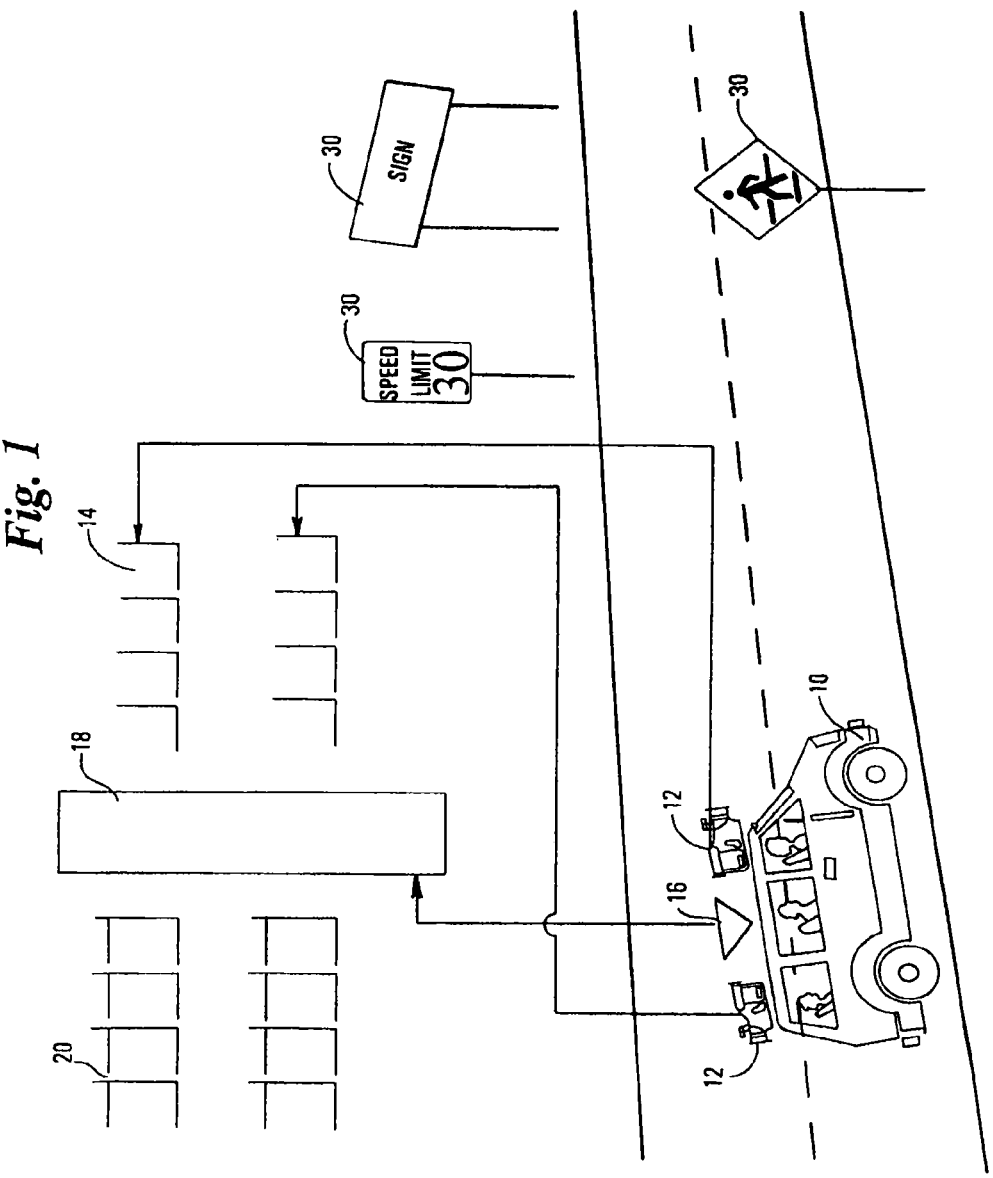
FIG. 1 is a capture vehicle used in a preferred embodiment of the present invention.

Referring to FIG. 1, an acquisition vehicle 10 is equipped with multiple video cameras 12 that generate a series of raw videostreams 14 representative of a road or street over which the acquisition vehicle 10 is traveling. A global positioning satellite (GPS) receiver 16 supplies location information that is combined with the raw videostream 14 by a processor 18 to generate a tagged videostream 20.

Figures 1, 14A:
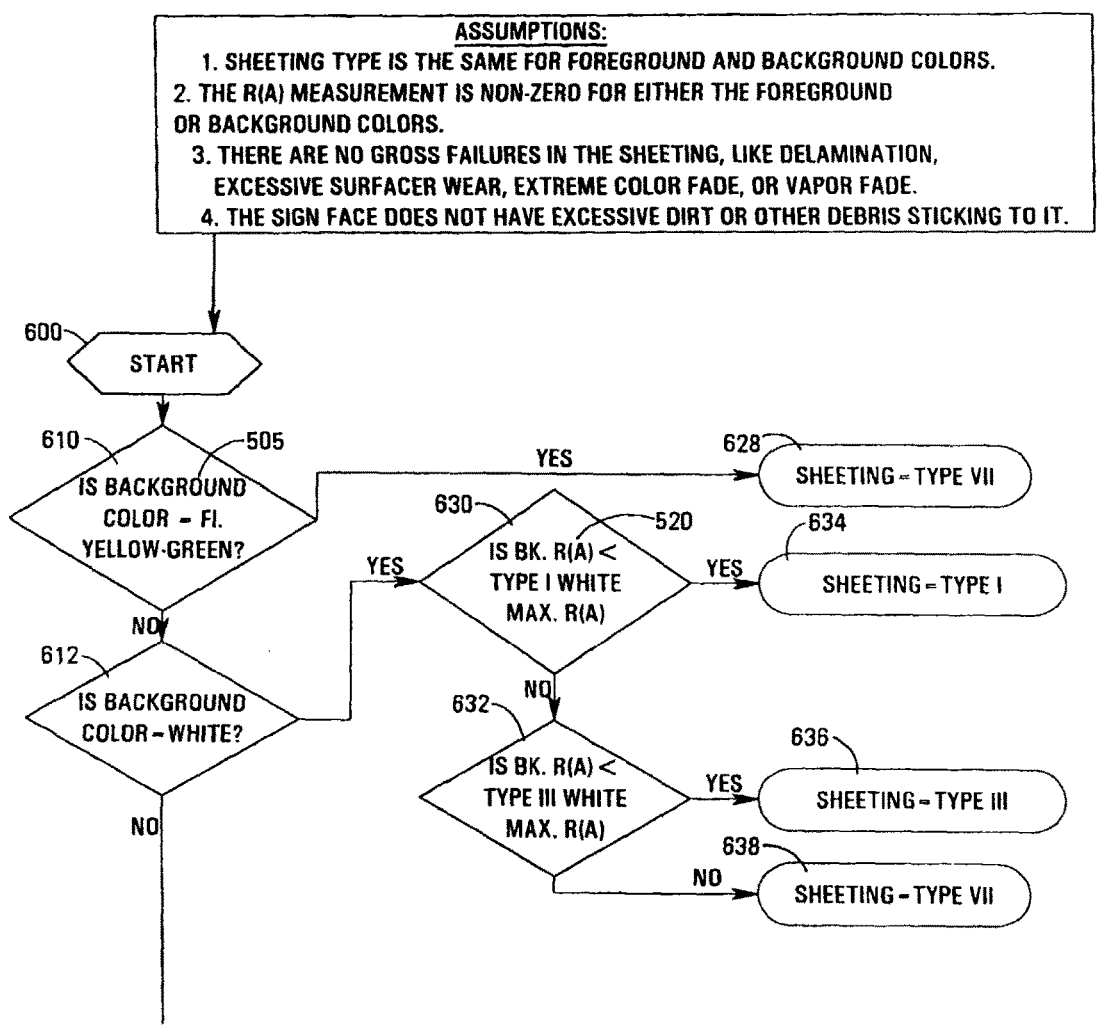
Figures 2, 14A:
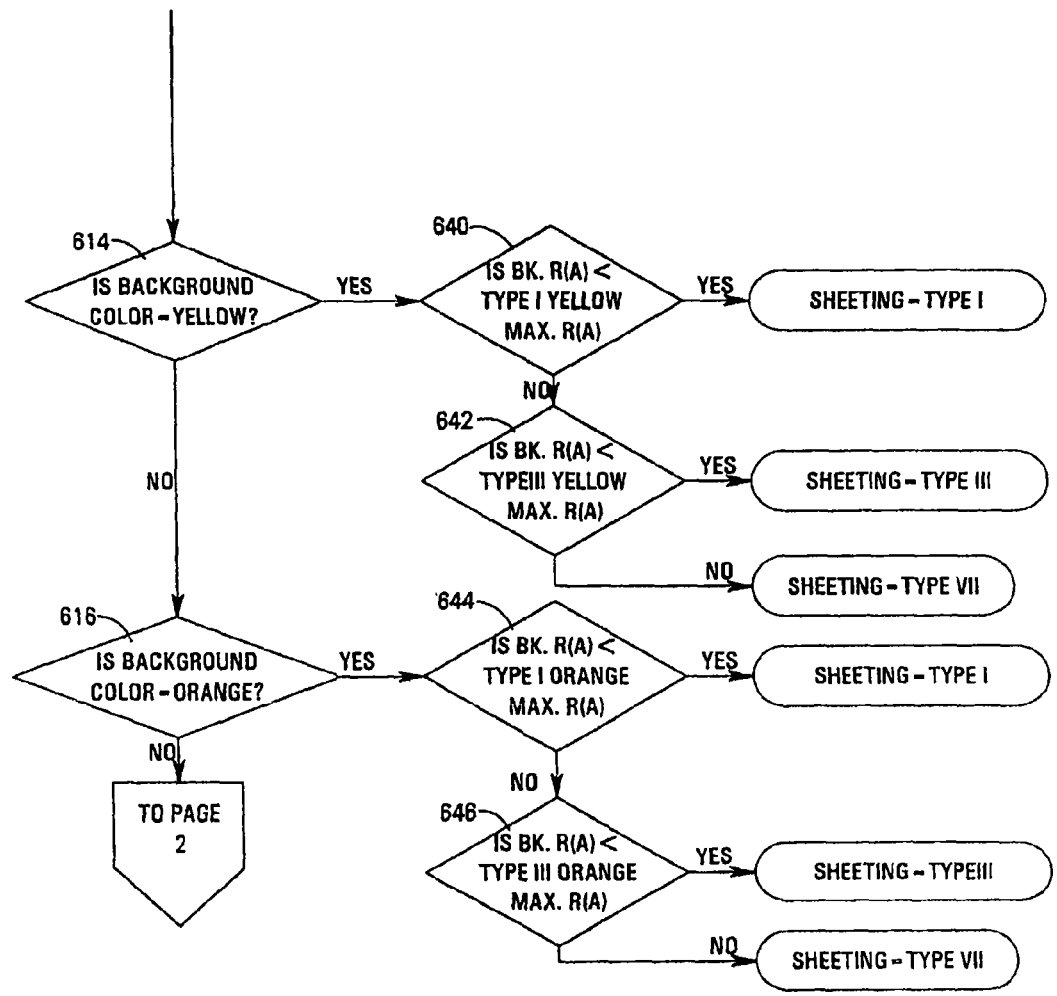

In one embodiment as shown in FIG. 2, the tagged videostream 20 is analyzed by a computer processor 22 to identify each road sign 30 and generate an asset management database 24 containing attribute and location information associated with each road sign 30. In an alternate embodiment, the identification of road signs 30 and generation of asset management database 24 is accomplished by the same processor 18 that tags the raw videostream 14. The details of this process are set out in U.S. Pat. No. 6,453,056, issued Sep. 17, 2002 to Laumeyer et al., which is hereby incorporated by reference.

Either concurrent with or subsequent to the identification of road signs 30 and generation of asset management database 24, the computer processor 22 evaluates that portion 32 of each video frame or image that depicts a road sign 30 to determine a set of color values 40, 42 for each of a plurality of colors on the road sign 32. A retroreflectivity value is generated for each color portion 34, 36 on each frame of the tagged videostream 20 containing the road sign 30 that represents a different color value 40, 42. Preferably, the values for retroreflectivity are determined by measuring the intensity of the signal for each color portion 34, 36. These values are then analyzed over the number of frames containing each color portion 34, 36 to arrive at the maximum retroreflectivity value 44, 46 that corresponds to the color value 40, 42 for each color portion 34, 36 of the road sign 30. These maximum retroreflectivity values 44, 46 will be the reference values used in the threshold algorithm from which sign sheeting classification will be determined.

There are three main types of sheeting recognized in the industry: 1) Type I, commonly called Engineer Grade; 2) Type III, commonly called High Intensity; and 3) Type VII, commonly called Prismatic (Prismatic is sometimes divided into two groups—Type VIIa called Diamond Grade VIP, and Type VIIb called Diamond Grade LDP). In order to remove the manual element of determining sheeting type and measuring retroreflectivity, the automated system of the present invention must accurately distinguish between these sheeting types. To accomplish this, the present invention utilizes the fact that all signs use the same sheeting type for foreground and background colors, that each road sign will have at least two colors and that the reflectivity for each color for each type of sheeting material has a relatively unique minimum initial retroreflectivity value. Most signs also have either White, Yellow or Orange colors as one of the colors on the sign. According to 3M, a manufacturer of reflective sheeting material, each color of the three sheeting types has a minimum initial retroreflectivity value. The following table lists the minimum values for common colors of each type:

| Color | Type I Min · $R_A$ | Type III Min · $R_A$ | Type VIIa Min · $R_A$ | Type VIIb Min · $R_A$ |
|---|---|---|---|---|
| White | 70 | 250 | 430 | 800 |
| Yellow | 50 | 170 | 350 | 660 |
| Orange | 25 | 100 | 200 | 360 |
| Red | 14.5 | 45 | 110 | 215 |
| Green | 9 | 45 | 45 | 80 |
| Blue | 4 | 20 | 20 | 43 |

This information is stored in a reflectivity/color database 50. The computer processor 22 accesses the database 50 using the maximum reflectivity value 44, 46 that corresponds to the color value 40, 42 for each color portion 34, 36 to determine the lowest possible sheeting type for each color. If the sheeting type is classified the same for all of the color portions 34, 36 for a given road sign 30, then the sheeting class 52 is established as that type and this information is preferably stored in the asset management database 24 along with other attributes of the given road sign 30. If there is a discrepancy in the classification of sheeting material between different colors, a subsequent analysis by the processor 22 using, for example, a neural network program, to incorporate other determining factors, such as time of day, shadow, direction that could affect the retroreflectivity of the lighter colors (white, yellow and orange) more than the retroreflectivity of the darker colors (red, green, blue). In general, retroreflectivity values for lighter colors are weighted more heavily in resolving any discrepancies in classification of sheeting material.

The system described herein acquires many data points along the desired roadway without specifically targeting any objects of interest. For a roadside sign, the specific geometry of the sign (its orientation with respect to the roadway) is not necessarily known, nor is it required. The retroreflectivity points determined along the roadway are generated for the "as placed" road sign. Road signs will display their best retroreflectivity performance (have the highest retroreflectivity values) at or near the normal vector for the sign face. Since the geometry of the as-measured sign is not known, the system chooses the highest retroreflectivity value for that sign as the value that will be used in the threshold algorithm for sign sheeting classification.

There are several factors that can cause retroreflectivity readings for signs to actually be lower than the values for the underlying sheeting type. For example, a sign that has a layer of dirt on the face will produce lower retroreflectivity numbers than usual. If these lower numbers are used in the threshold comparison algorithm, an incorrect sheeting type may result. These systematic errors can be removed by analyzing the retroreflectivity profile for the sign.

Figure 13:
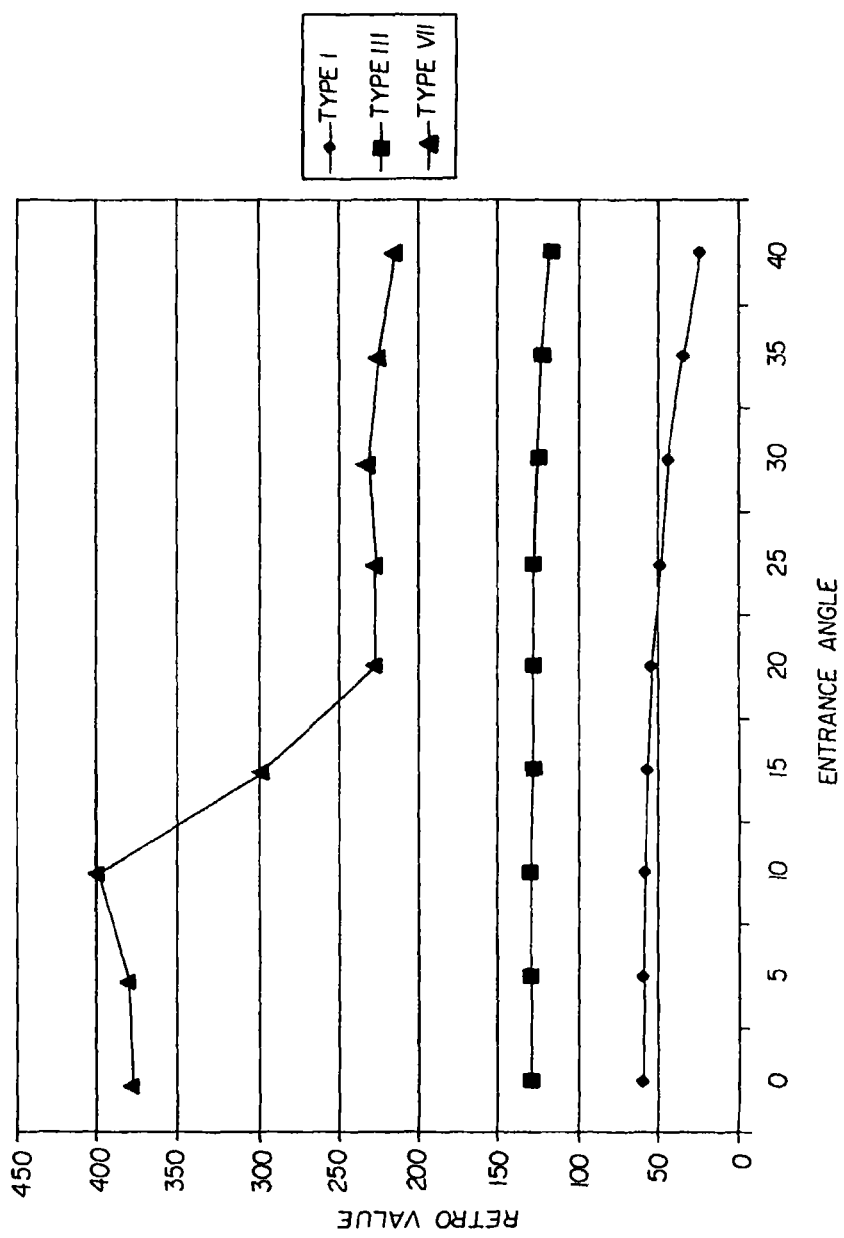
FIG. 13 is a graphic representation of the retroreflectivity performance for white sheeting for the three main types of sign sheeting.

Sign sheeting types vary by the intensity of light that is reflected, but they also have reflective characteristics that give them unique signatures. FIG. 13 shows the profiles for Type I, Type III, and Type VII white sign sheeting types. Note the unique profiles for the three sheeting types. The preferred embodiment of the present invention, due to its ability to utilize multiple retroreflectivity points, can determine sheeting type by matching the as-measured profile with a uniformly reduced (where the entire curve is multiplied by a scaling factor that is less than one) characteristic curve that best correlates to the as-measured profile. This correlation step will establish the "best fit" performance curve based on the shape of the curve, without consideration for the magnitude of the curve. This "uniform reduction" of the sign sheeting performance curve allows the proper sheeting type to be determined, thus overcoming the problem with signs that have some type of surface anomaly. The performance curve correlation described above can be used in one of two ways—either as a validation of the proper determination of sheeting type from the threshold algorithm or as one of the qualification criteria prior to performing the threshold algorithm.

The sheeting types are all manufactured with multiple layers. In order for the present invention to accurately compute retroreflectivity for purposes of determining sheeting type of a given road sign, it is also necessary for the system to recognize gross sheeting failures like extreme color fade, de-lamination and vapor fade (darkening of the daylight appearance of the sheeting due to the corrosion of the metal sign backing). These gross failures will impact $R_A$ measurements of the sheeting. Preferably, the sheeting determination system described herein tests for the absence of these gross failures prior to making any $R_A$ measurements as part of the process of categorizing sheeting type.

Figure 11:
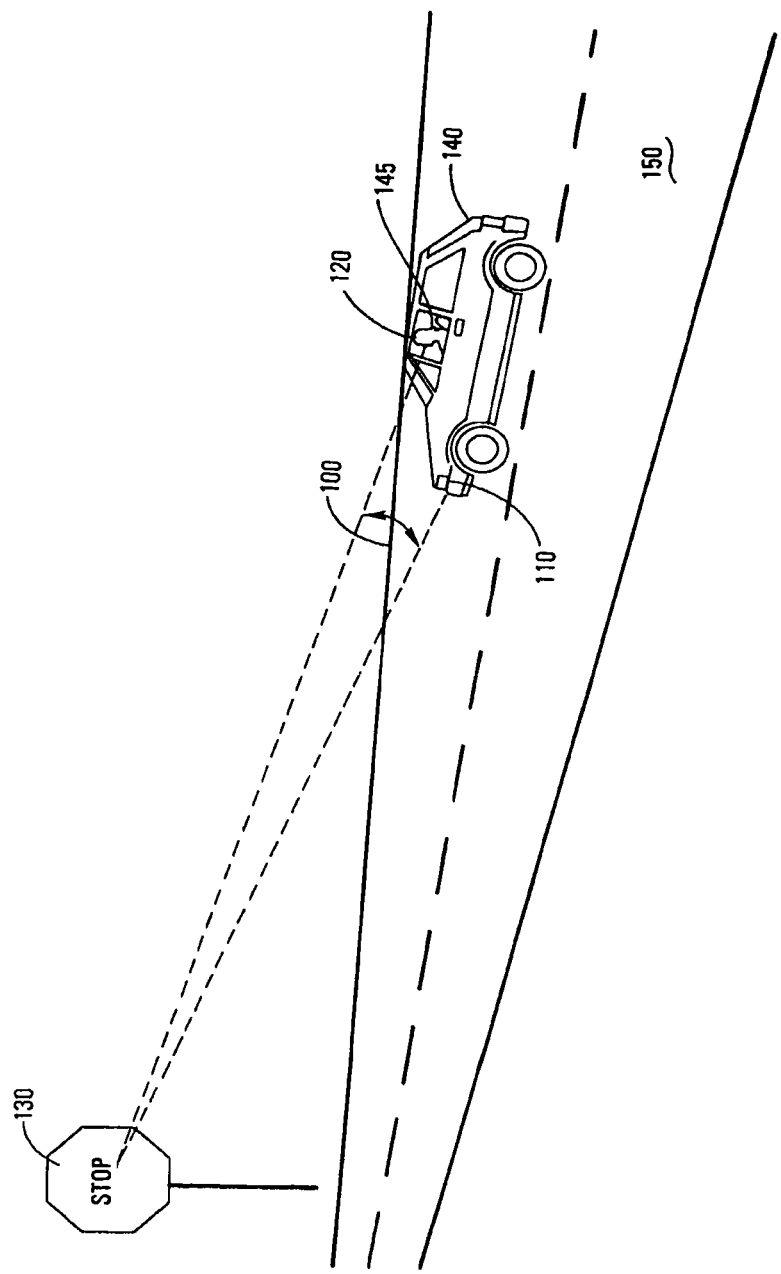
FIG. 11 depicts the concept of observation angle (i.e., angle between incident light from a light source and an human observer (or light sensor), of the light as reflected from the face of a reflective asset) in the context of a conventional passenger vehicle traversing a vehicle pathway and where light from the vehicle reflects from a stop sign to the vehicle operator (shown in ghost).

Retroreflectivity, designated as "$R_A$" generally (and from time to time in this disclosure), varies according to two key parameters, observation angle and entrance angle. Observation angle 100 (See FIG. 11) is the angular displacement between a light source 110 and a light sensor 120, as measured from an object face surface 130. In the case of a vehicle 140 driven by vehicle operator 145 moving along a highway 150, observation angle 100 is defined by the distance of the vehicle 140 from a sign face surface 130, the placement of the light source (headlights) 110 on the vehicle 140, and the position of the light sensor (eyes of the vehicle operator) 120 of the vehicle 140.

Figure 12:
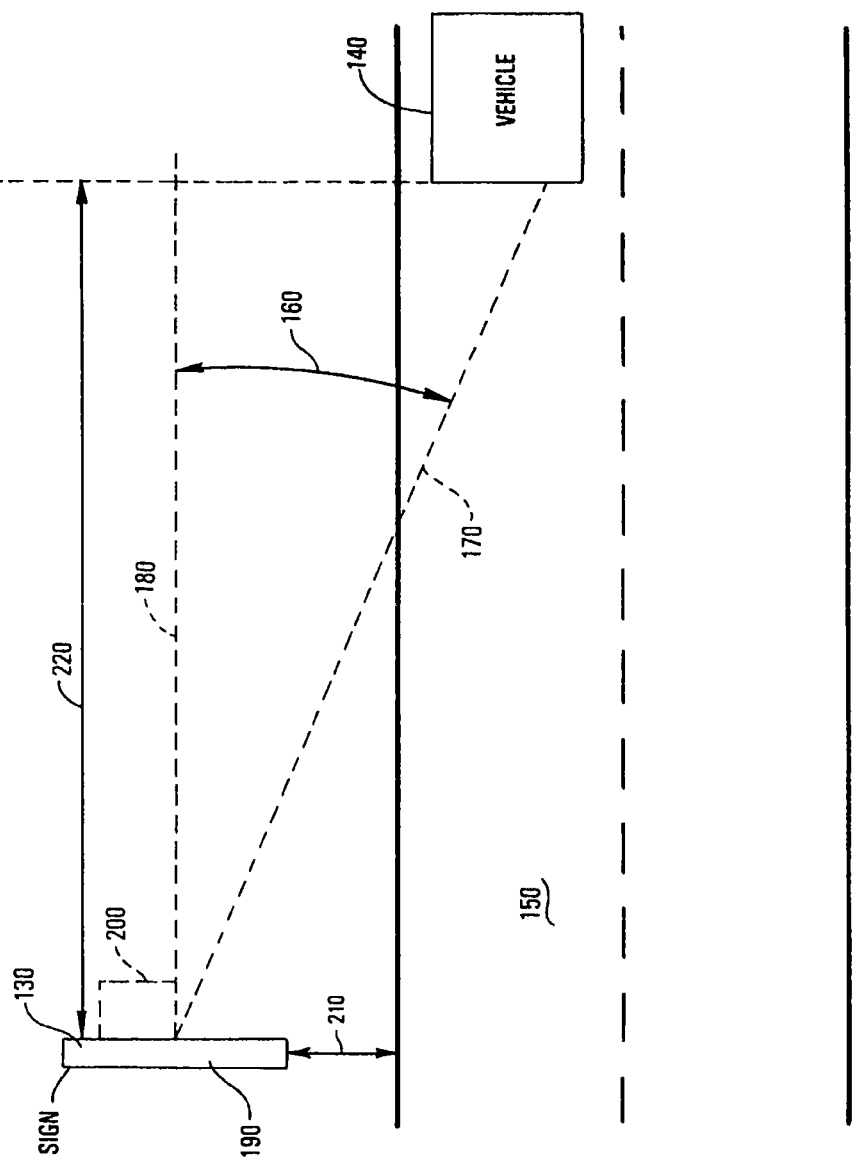
FIG. 12 depicts the concept of entrance angle (i.e., angle between incident light from a light source mounted to a vehicle and a normal vector relative to the substantially flat face of a reflective surface disposed adjacent a vehicle pathway).

Entrance angle 160 (See FIG. 12) is defined as the angular displacement of the incident light 170 relative to the normal vector 180 from the object face surface 130. Entrance angles are impacted by the angular position 200 of a sign 190 relative to the highway 150, the sign 190 lateral distance 210 from the highway 150, and the distance 220 of the vehicle 140 from the sign 190. The inventors hereof are believed to be the first persons to successfully decrease the complexity and increase the efficiency of determination of $R_A$ in the field.

The method of automated determination of $R_A$ (See FIGS. 3 and 4) preferably utilizes a plurality of subsystems located on/in a capture vehicle 225. These subsystems include a light intensity measurement system 230, a vehicle positioning system 240, a color image capture system 250 and a data recording system 260. The light intensity measurement system 230 preferably includes a high output light source 270, a light intensity sensor 280 and an intensity measurement system control 290. A plurality of intensity measurements 300 are generated by the intensity measurement system 230 in response to the repeated strobing of the high output light source 270. The vehicle positioning system 240 preferably includes a GPS receiver 310, an inertial navigation system 320, a distance measuring instrument 330 and a master clock 340. A position measurement 350 is generated by the vehicle positioning system 240. The color image capture system 250 preferably includes a stereoscopic camera pair 360, iris controls 370 and image capture control 380. The image capture system 250 generates a digital imagery stream 390.

Figure 5:
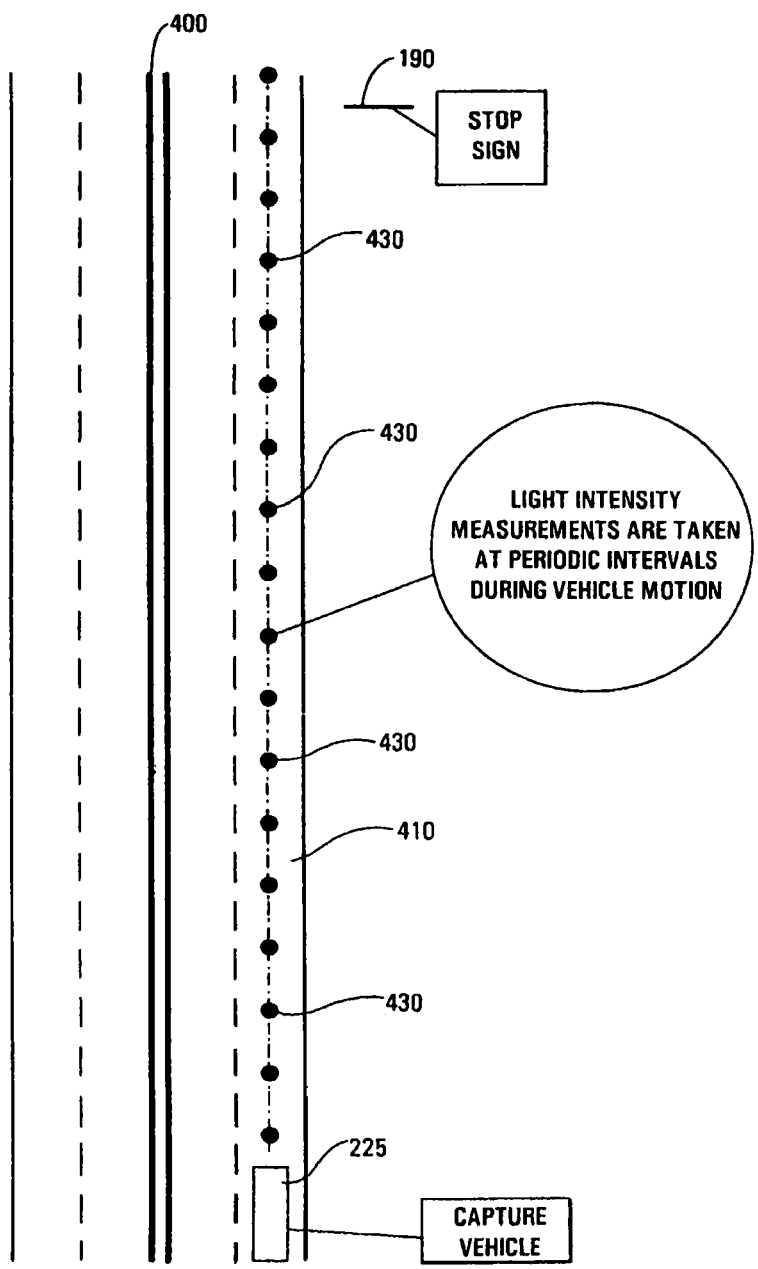
FIG. 5 is a plan view of a divided multi-lane vehicle pathway and depicts how periodic light intensity measurements may be made as a vehicle traverses the vehicle pathway over time and the discrete locations where such periodic light intensity measurements are performed by a data acquisition vehicle operating in accordance with the present invention.
Figure 6:
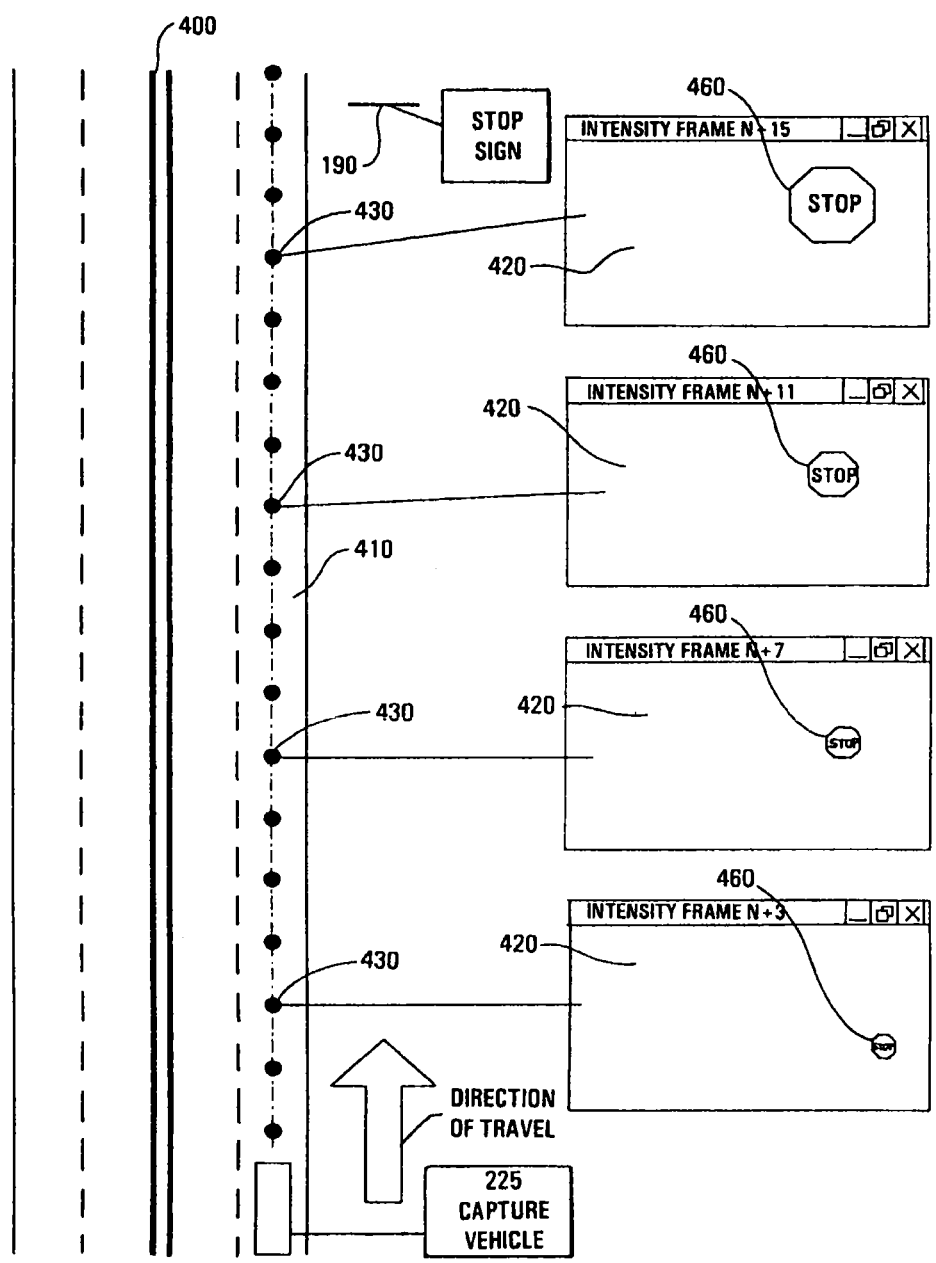
FIG. 6 depicts four digital frames of data as captured by the intensity sensor at various discrete locations along the vehicle pathway depicted in FIG. 5.

The data required for the automated determination of $R_A$ is accumulated while traversing a highway 150 with the capture vehicle 225 (See FIGS. 5 and 6). The capture vehicle 225 is shown on a 4-lane divided highway 400 with the capture vehicle 225 located in a proximate lane 410 to the stop sign 190. Preferably, a series of reflected light intensity frames 420 are generated at a constant measurement interval 430 as the capture vehicle travels along the highway 150.

Characterization of sign 190 $R_A$ preferably utilizes the data recording system 260 to create a single tagged videostream 440 from the reflected light intensity frames 420, position measurements 350 and digital imagery 390 for each capture event 430 (See FIGS. 3, 5, 6, 7, and 8). A computer processor 450 identifies an object of interest 460 in a portion of the intensity frame 420 and determines the object of interest attributes 465 associated with that object of interest. Preferably, the objects of interest are identified from the digital imagery stream 390 generated by the color image capture system 250 in the manner as taught by U.S. Pat. No. 6,266,442. Alternatively, other techniques known in the art for isolating an object of interest in a videostream can be used. Preferably, the computer processor 450 correlates the portion of an image frame of the digital imagery stream 290 with a similar portion of the intensity frame 420 containing the object of interest 460.

For each object of interest 460, a background intensity measurement 470 and a foreground intensity measurement 480 is generated. Using an intensity algorithm 490, a light intensity sensor characterization 275 and a look-up-table 475, the computer processor 450 determines a background luminance value 500 and a foreground luminance value 510. Based on the background luminance value 500, the foreground luminance value 510, a characterization of light source wavelength 540, the background sheeting color 505 and the foreground sheeting color 506 the computer processor 450 characterizes a background $R_A$ 520 and a foreground $R_A$ 530 which are preferably reported separately for that object of interest.

Figure 9:
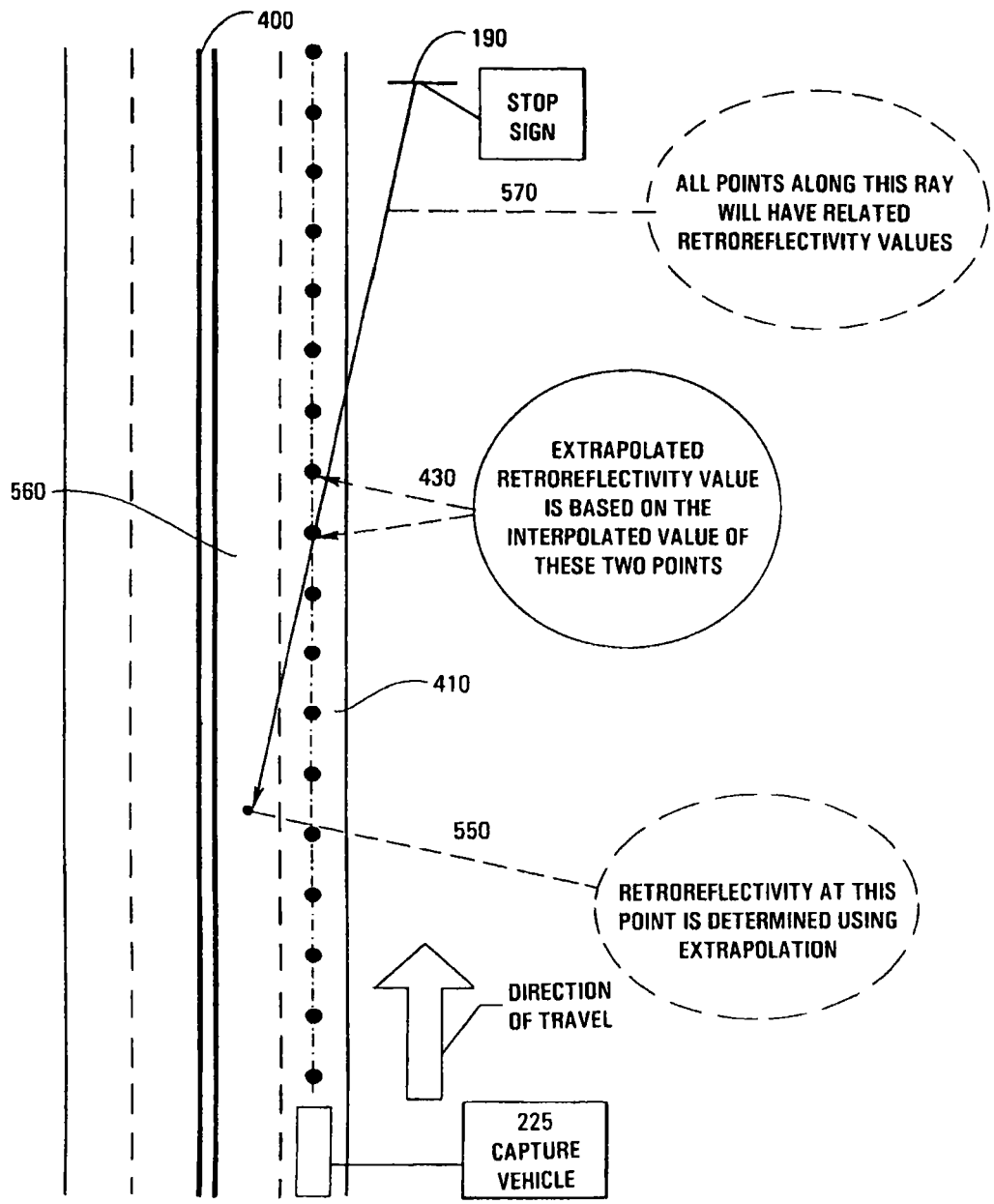
FIG. 9 depicts a preferred methodology for creating a retroreflectivity profile for all lanes and locations adjacent a vehicle pathway for a single reflective asset or sign which retroreflectivity profile is based upon a single pass of a data acquisition vehicle over the vehicle pathway.
Figure 10:
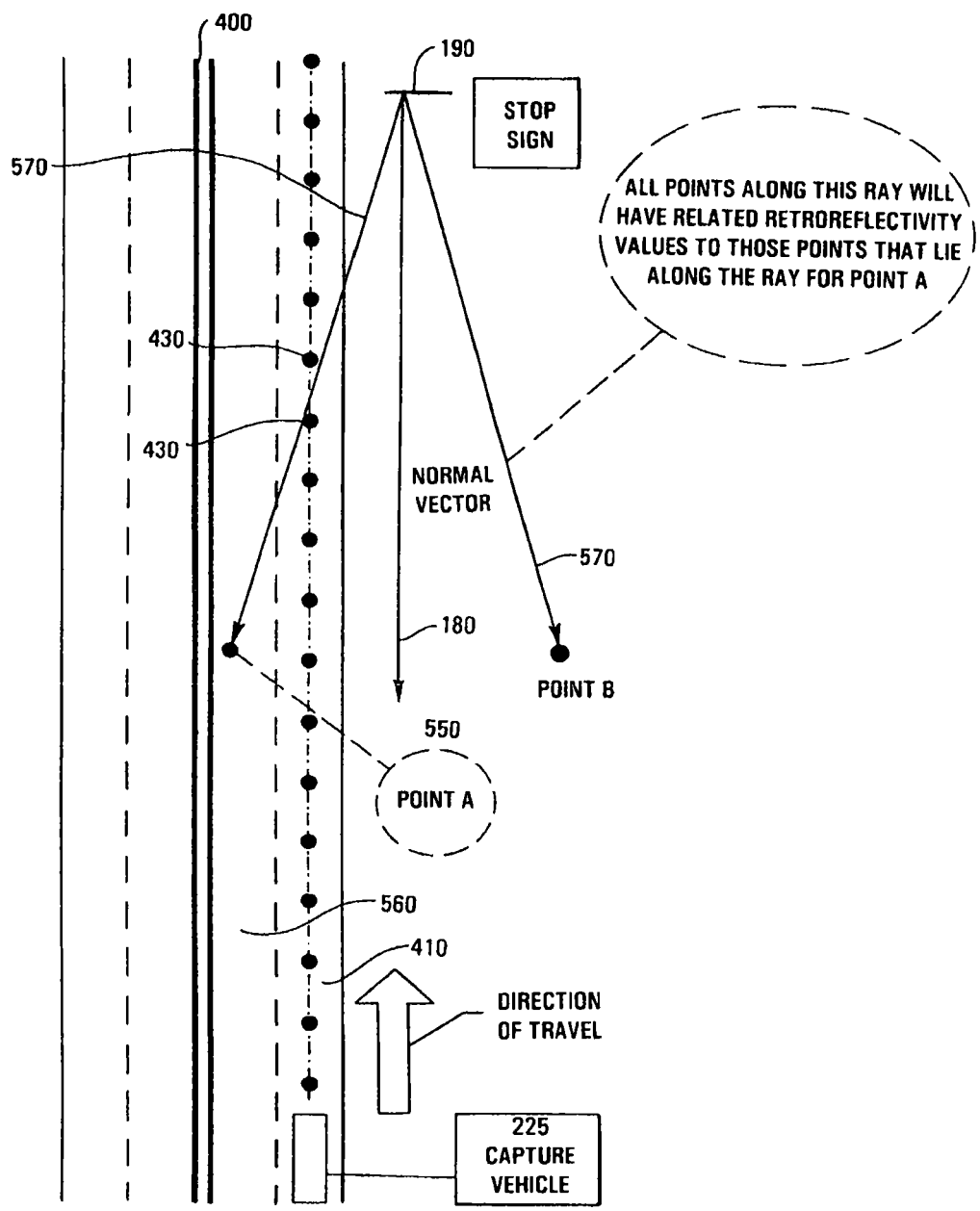
FIG. 10 illustrates the facts that the normal vector of a reflective asset and the sheeting type of such a reflective asset create symmetry that may be used to determine retroreflectivity values along all rays (or vectors) that have the same relative angle to the normal vector of the reflective asset.

The automated determination of multiple $R_A$ values for a given object of interest 460 allows for the extrapolation of $R_A$ values at an unmeasured viewing point 550 for an object of interest, such as a sign 190 (See FIGS. 9 and 10). In this example, the unmeasured viewing point resides in a nontraversed lane 560. The computer processor 450 defines an undetermined retroreflectivity ray 570 for unmeasured viewing point 550. Using interpolated values, the computer processor 450 determines an $R_A$ value for unmeasured viewing point 550 and any point located along undetermined retroreflectivity ray 570.

Pursuant to the teaching of the present invention, a method and apparatus for determining retroreflectivity of relatively flat surface portions of objects disposed adjacent a highway 150 traversed by a vehicle 140 are taught, enabled, and depicted. The present invention may be utilized to detect and determine a retroreflective surface of interest disposed in a scene of non-retroreflective surfaces. That is, at least one object face surface 130 which exhibits retroreflectivity over at least a relatively narrow conical volume of magnitude of several degrees from a normal vector 180 originating from said object face surface 130.

In accordance with the present invention, a determination of the retroreflectivity of objects adjacent a highway 150 preferably includes providing: (i) position measurements 350 of a capture vehicle 225; (ii) precise position of the object of interest 460, or sign 190; (iii) intensity measurements 300 from a high output light source 270 and light intensity sensor 280 at measurement intervals 430 along said highway 150. Thus, a single-pass along the highway 150 by the capture vehicle 225 operating the light intensity measurement system 230, vehicle positioning system 240, image capture system 250 and data recording system 260 taught herein eliminates many shortcomings of the prior art and allows a single vehicle operator to conduct virtually continuous data measurement and acquisition of objects of interest 460 disposed adjacent a highway 150, at capture events 430 on said highway 150, without disrupting or interrupting other vehicle traffic traversing said highway 150.

Figure 3:
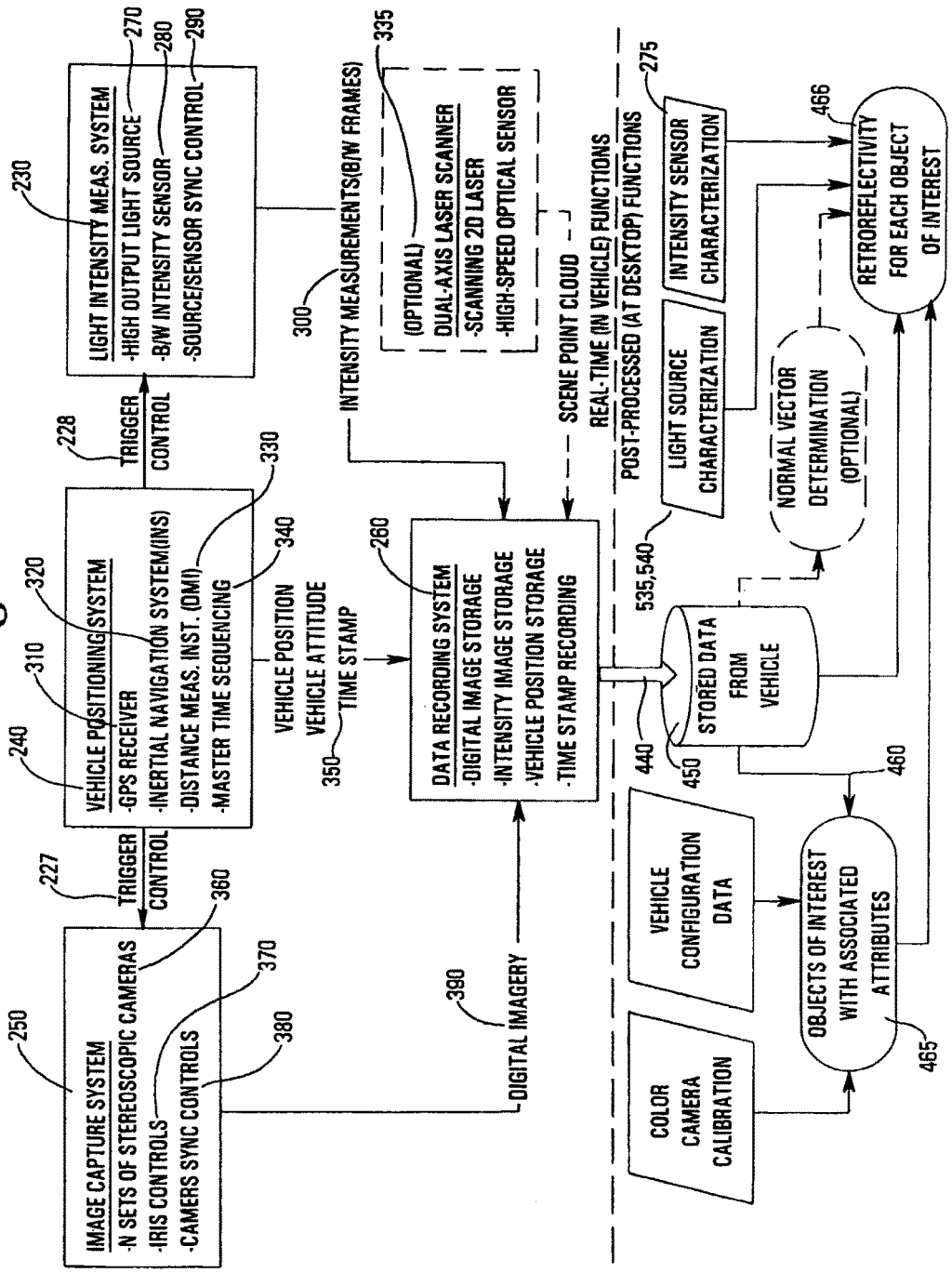
FIG. 3 depicts a block diagram of the systems, subsystems and processes for capturing and processing roadside information from a moving platform in order to compute retroreflectivity according to the teaching of the present invention, wherein the arrows connecting the blocks of the diagram illustrate the connections between the systems and subsystems for computing $R_A$ for each reflective asset recorded by the system of the present invention.

FIG. 3 shows a block diagram of the on-board systems and the desktop systems required to record a tagged videostream 440 and create sign $R_A$ profiles 590 for various signs 190 along a highway 150. The vehicle positioning system 240 contains all of the equipment to precisely locate the capture vehicle 225. All location information is synchronized with a master clock 340 preferably associated with a computer processor 450, which allows other data types to be merged with the vehicle location information at later stages in the post-processing. All of the on-board systems utilize the same master clock 340 information, thus allowing any events (image capture system 250, intensity measurement 300, and trigger controls 227, 228) to be correlated to the precise vehicle location and attitude during real-time, near real-time, or post-processing of the data acquired by the capture vehicle 225.

The image capture system 250 consists of at least one set of stereoscopic cameras 360 that gather digital imagery along the highway 150. Each capture event is combined with time stamp information from the vehicle positioning system 240 which also provides trigger control 227 for the image capture system 250 and trigger control 228 for the light intensity measurement system 230. These images and associated time stamps are later combined with photogrammetry to create objects of interest 460 and their associated attributes 465.

The light intensity measurement system 230 preferably consists of at least one high output light source(s) 270 and the associated light intensity sensor(s) 280. The precise control for these items is contained within the light intensity measurement system 230, and master time sequencing instrument 340 information received from the vehicle positioning system 240 (or computer processor 450) is combined to create a tagged videostream 440 so precise vehicle information can be utilized during post-processing.

The data recording system 260 is constantly monitoring control information from the other three on-board systems and records the necessary information. No post-processing is performed in the data recording system 260. As computer power increases in the future, one skilled in the art could produce a system whereby most, if not all, of the post-processing functions were performed in the capture vehicle 225, perhaps even in real time. The inventors can imagine several uses for the production of real-time information from the image capture system 250 in the future, but the cost of obtaining such information with today's computing power makes this option prohibitively expensive today.

The lower half of FIG. 3 shows the functional blocks for data post-processing. There are two main functions—the creation of objects of interest 460 and their associated attributes 465, and the determination of retroreflectivity for each object of interest 460. There are many methods for creating objects of interest 460 from digital imagery, a few of which are discussed in this disclosure. The specific steps required to compute $R_A$ are outlined in the discussion below.

Figure 4:
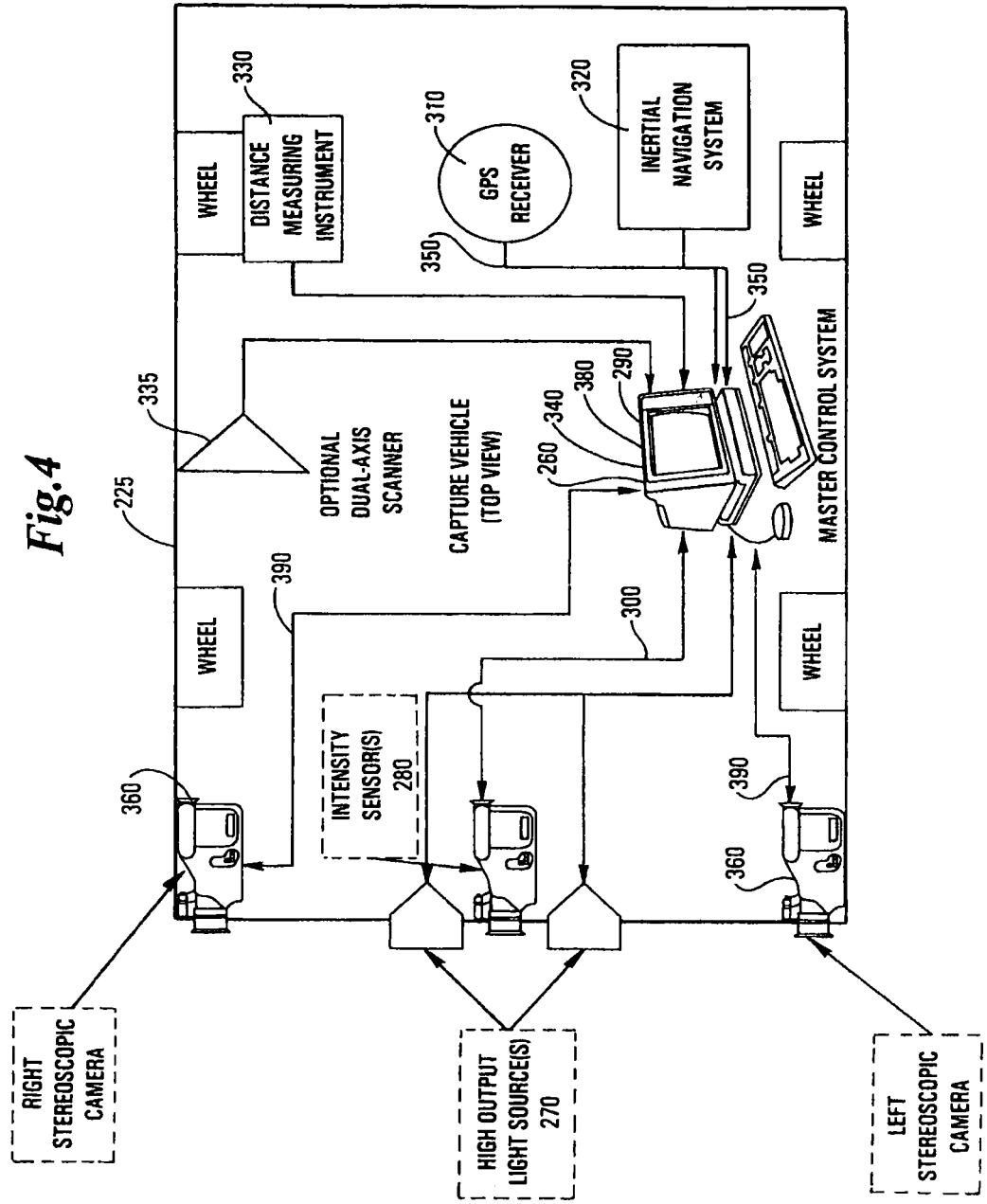
FIG. 4 depicts in diagram form, a preferred configuration of a sensor suite for use with a four-wheeled vehicle and the interconnections and couplings between the physical subcomponents of a system designed according to the present invention.

FIG. 4 shows a typical configuration within a capture vehicle that is capable of producing data and imagery to create digital representations of objects of interest 460 and objects of interest retroreflectivity 466. The distance measuring instrument (DMI) 330, GPS receiver 310 and inertial navigation system (INS) 320 constitute the vehicle positioning system 240. Not all of these components are necessary to obtain the desired results, but better precision, and therefore more meaningful data, are produced if all three components are included.

The high output light source(s) 270 and light intensity sensor(s) 280 constitute the light intensity measurement system 230. These components make it possible to gather on-the-fly information for a desired highway 150 to allow the computation of object of interest retroreflectivity 466, as well as create a full 3-D sign $R_A$ profile 590 for those same objects of interest 460.

The stereoscopic cameras 360 constitute the digital imagery system 390 that allows for the creation of objects of interest 460 and their associated attributes 465 during post-processing. More than one set of stereoscopic cameras 360 can be employed, thus increasing the accuracy of positional measurements for objects of interest 460. Other, non-stereoscopic imaging systems could also be employed with little or no change to the vehicle positioning system 240 or to the light intensity measurement system 230.

FIG. 5 shows the top view of a 4-lane divided highway 400 with a stop sign 190. The capture vehicle 225 is traveling in the proximate lane 410 to the stop sign 190 and makes intensity measurements 300 at capture events 430 while traveling the depicted route. The techniques described herein will allow a retroreflectivity value for this stop sign 190 to be computed for any point along the 4-lane divided highway 400, independent of whether the intensity measurement 300 was made at that point and also independent of whether the capture vehicle 225 actually drove over that point.

It should be noted that intensity measurements 300 are made continuously while the capture vehicle 225 is in motion, thus requiring no prior knowledge of either the positions or the existence of signs.

FIG. 6 shows some typical reflected light intensity frames 420 as captured by the light intensity sensor 280 at various discrete locations along the roadway. These reflected light intensity frames 420 are the result of the high output light source 270 being energized (or flashed) while each reflected light intensity frame 420 is captured by one or more light intensity sensors 280. Since most of the objects in the scene are not reflective, and due to the high setting of the threshold range in the light intensity sensor(s) 280, the reflected light intensity frames 420 will actually show very few objects. For effective luminance results throughout a wide range of retroreflective materials, more than one light intensity sensor 280 may be required in order to get enough levels of gray within the active part of the visible spectrum. When multiple light intensity sensors 280 are required or used, they may each have different threshold ranges and each thus detect luminance values in different parts of the desired luminance ranges.

In order to compute retroreflectivity ($R_A$), one needs to know the luminance of the reflected energy. Luminance (expressed in candelas per square meter, or $cd/m^2$) will vary according to the intensity sensor characterization profile 275 of the light intensity sensor(s) 280 and the color of the material from which light is reflected.

Most roadway signs 190 contain text and/or symbols overlaid on a background. To ensure maximum visibility during day and night conditions, the colors of the foreground information (text and/or symbols) are chosen to have maximum day and night contrast with the background material. The techniques taught herein allow the retroreflectivity of roadway signs 190 to be determined for both foreground and background materials. Computing both the foreground 530 and background retroreflectivity 520 for each object of interest 460 allows us to ensure that the proper nighttime contrast is achieved for roadside assets. For example, a stop sign 190 with a red background and white lettering can provide good daytime contrast between the text and the sign background. But if these two materials display very similar retroreflectivity characteristics, their nighttime contrast will be minimal, thus rendering the sign ineffective during nighttime conditions.

Figure 7:
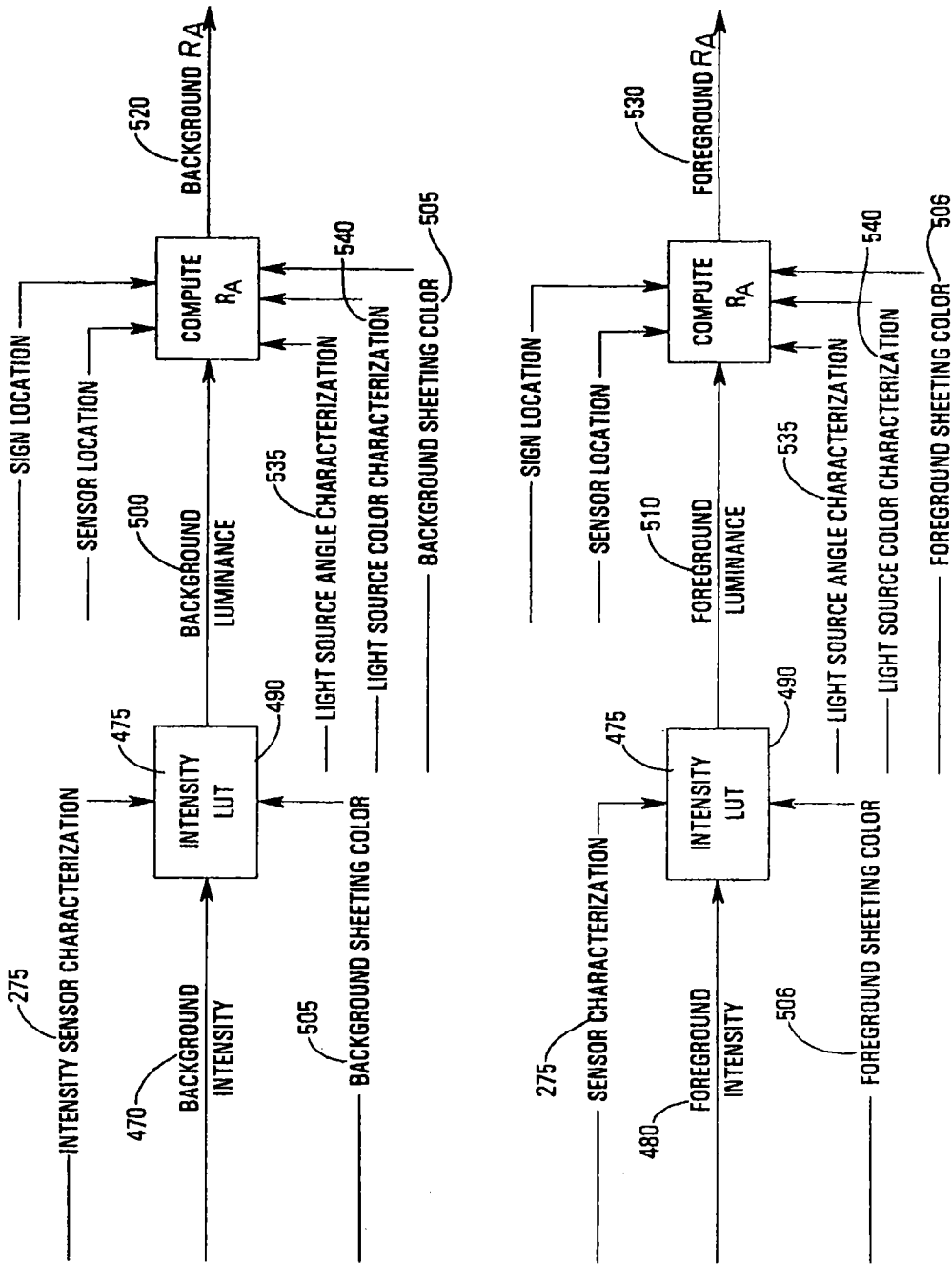
FIG. 7 depicts a flowchart showing the steps required to convert intensity measurements into foreground and background retroreflectivity for a single reflective asset.

FIG. 7 shows a block diagram of the steps required to transform intensity measurements 300 into foreground luminance values 510 and background luminance values 500. First, a black and white camera is preferably used as a light intensity sensor 280 to maximize the sensitivity of intensity measurements 300 (intensity will be determined from the gray value of the corresponding pixels). Think of an intensity measurement 300 as intensity values for N discrete points within the scene, where N corresponds to the number of pixels in the light intensity sensor's 280 array. For a light intensity sensor 280 that has a resolution of 640×480 pixels, there are 307,200 discrete intensity values for each intensity sensor measurement 300. Although the preferred embodiment utilizes an intensity sensor measurement 300 in the form of an array of discrete pixel intensity values, preferably a single pixel intensity value is selected and utilized for the automated determination of a corresponding retroreflectivity value. Alternatively, an average or other combination of a group of pixel intensity values could be utilized for the automated determination of a corresponding retroreflectivity value. Intensity values will vary according to the color of the reflected light, since not all colors of incoming light excite the light intensity sensor 280 pixels in the same way. By knowing the background or foreground color of the object of interest 460 along with the light intensity sensor's 280 ability to sense, or the light intensity sensor's 280 profile for a particular color, the intensity value 300 for a particular color can be converted into a luminance value. Light intensity sensor 280 characterization is essential for high precision computations since N photons of a given particular color (or wavelength) of light will represent a different gray value (intensity level) in the sensor than N photons of another color (or wavelength) of light. The look-up-table (LUT) 475 shown in FIG. 7 is a digital table stored in memory that uses the indexes of intensity (a single gray level value from the intensity measurement 300) and sheeting color to determine the luminance. The light intensity sensor characterization 275 is empirical information about the light intensity sensor 280 that is used to create the LUT 475. The same LUT 475 is used for computing foreground 510 and background luminance values 500.

The reader should note and appreciate that luminance is strictly a measure of the reflected light, while retroreflectivity (or $R_A$, expressed in $candelas/lux/m^2$) is a measure of the reflected light with respect to the incident light for that object. FIG. 7 shows the information needed to accurately convert luminance to $R_A$: sensor location, object location, light source characterization, and color of reflective material. For less precise $R_A$ computations, a subset of the aforementioned characteristics can be utilized. For example, if a uniform light source (equal intensity throughout the scene), columnated light reflected from the surface of the object of interest 460, and a known distance 220 between the object of interest 460 and the light intensity sensor 280 are all assumed, then the sheeting color and luminance value may be used to determine a rough approximation (within 20%, for example) for $R_A$.

To obtain the highest quality $R_A$ calculations, all of the data shown in FIG. 7 should be utilized. The characterization of light source angle defines the amount of light emitted from the high output light source 270 throughout the source's field of view. Due to the limitations of lamp design and their associated reflectors, most semi-uniform light sources will have their greatest intensity at or near the normal vector for the light source. Since the high output light source(s) 270 are not aimed at objects of interest 460, the part of the incident light beam that is striking the object of interest 460 when the intensity measurement 300 is captured must be determined. Light source angle characterization is a process whereby empirical data from the light is modeled to establish the light intensity for numerous discrete vectors from the center of the light. When intensity values are determined for a discrete point in the scene (from the object's face surface 130), the light intensity sensor 280 location and heading, as well as the object of interest 460 location, are used to determine which light vector emanating from the light source was responsible for the resulting intensity measurement. The characterization of light source angle therefore, is a look-up-table where an object of interest's 460 angular displacement from the normal vector 180 for the high output light source 270 is converted to a light intensity for the associated vector.

Since the beam from the high output light source 270 is diverging, objects of interest 460 farther from the origin of the light will receive less incident radiation than those objects of interest 460 closer to the light. The characterization of light source angle is constructed at a few discrete distances from the light. Simple geometry can be used to compute the incident radiation (using an interpolation method for an actual distance between two discrete distances in the characterization of light source angle) hitting the actual object of interest 460 based on the empirical data from the characterization of light source angle.

Figure 8:
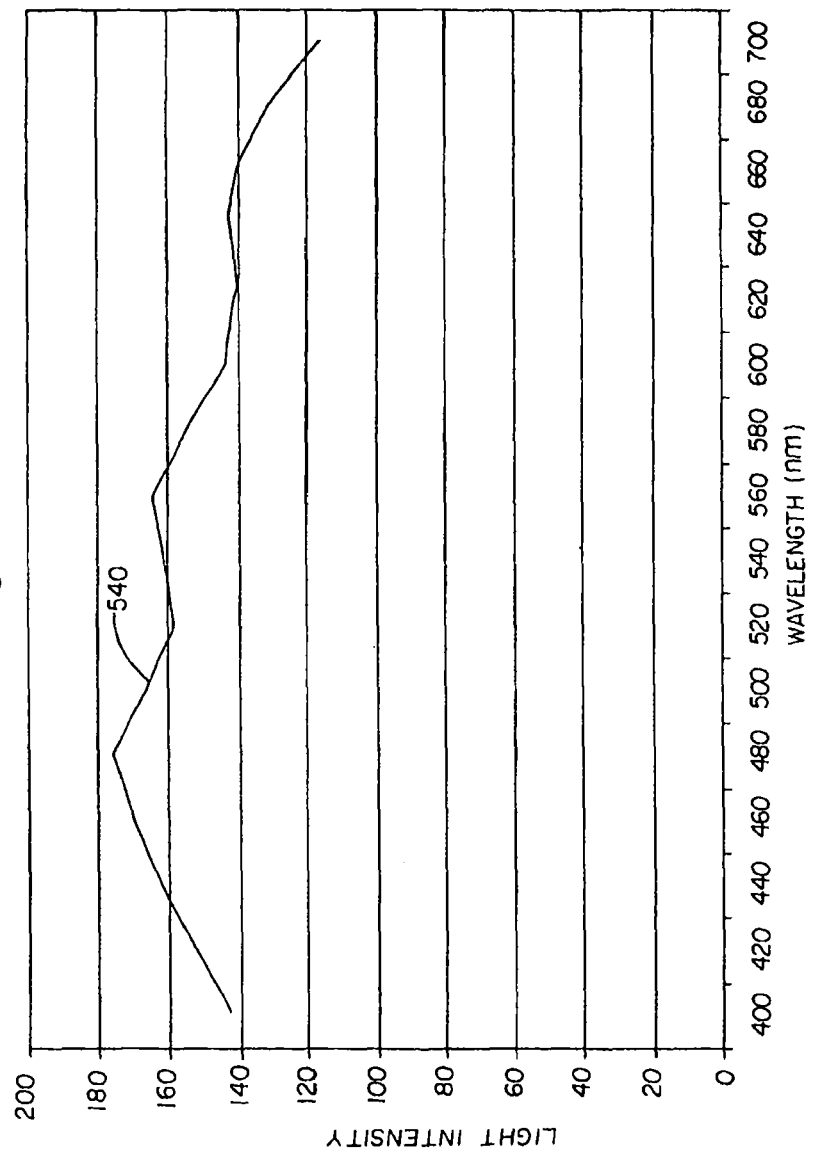
FIG. 8 depicts a typical light source intensity profile over the visible electromagnetic spectrum, which illustrates how different wavelengths of electromagnetic radiation possess different light intensities.

The preferred high output light source 270 is a uniform full-spectrum (visible spectrum) light. In practice, this light source will not emit the same intensity for all wavelengths of visible light. One variable of light source color characterization that should be considered is the output profile of the light throughout the visible spectrum. FIG. 8 shows a typical full-spectrum light source output profile. Note that the intensity in the blue area (400-500 nm) of the spectrum is stronger than in the red area (600-700 nm). This profile specifies the amount of light energy (number of photons) emitted for a given frequency. Since $R_A$ depends on the intensity of the incident light, the light source color characterization 540, light source angle characterization 535, background sheeting color 505 and foreground sheeting color 506 must be combined to determine how the background luminance value 500 and foreground luminance value 510 is converted to $R_A$ (i.e., what percent of the incident photons of the foreground/background color were reflected back to the sensor).

The divergence pattern for the light source may have different profiles for various portions of the visible spectrum. In practice, a separate light source angle characterization profile may be required for each possible foreground and background color of any given object of interest 460.

A preferred high output light source 270 is of the type set forth in the attached installation and operation guide entitled "StrobeGuard™ High Intensity Obstruction Lighting System, Model No. SG-60," manufactured by Honeywell, Inc. In order to create a useful sign $R_A$ profile 590 for an object of interest 460, intensity measurements 300 for frequent capture events 430 along a highway 150 while the capture vehicle 225 is in motion. For example, at vehicle speeds of 50 miles per hour, intensity measurements 300 should be taken at a rate of at least two per second. The StrobeGuard™ SG-60 model has a recharge time of about 1.5 seconds between successive flash events. As a result, one SG-60 light will not provide enough flash events per second to allow an adequate number of intensity measurements 300. In order to meet the requirements of two flash events per second for a capture vehicle 225 traveling at 50 miles per hour, three of the StrobeGuard™ SG-60 units would need to be fired in a synchronized, round-robin pattern to obtain enough trigger events.

The light intensity measurement system 230 described herein attempts to remove observation angle 100 as an $R_A$ variable. This is done by keeping the offset between the high output light source(s) 270 and light intensity sensor(s) 280 as low as possible. As mentioned previously, an $R_A$ profile of a simulated roadway 580 can be computed, even though the intensity was not measured at every point and even though the capture vehicle 225 did not drive over every point. First, it is critical that the geometry of $R_A$ is understood. Reflective materials like sign sheeting are designed to project near-columnated light back toward the light source. If a perfectly columnated light being reflected from the object of interest 460 being measured and a zero observation angle are assumed, the $R_A$ values for all discrete locations along a ray projected from the object will be identical.

FIG. 9 shows how to compute $R_A$ for any discrete location along a 4-lane divided highway 400. The $R_A$ value for the desired point will be based on the $R_A$ value that lies along the pathway traveled by the data acquisition vehicle 225. To compute this "reference $R_A$ value" (the $R_A$ value for a discrete location on or along a vehicle path), an undetermined retroreflectivity ray 570 is drawn from the desired location to the face of the reflective asset. The discrete location where the undetermined retroreflectivity ray 570 intersects the vehicle path will be used as the reference $R_A$ value. Since the discrete location on the vehicle path will always lie between two measured locations where intensity measurements 300 were made, the reference $R_A$ value is computed by interpolating the two closest (in distance) $R_A$ values along the vehicle path. As used herein, interpolate has the usual and typical meaning. It will be understood that interpolation consistent with the present invention can involve interpolation followed by extrapolation and shall also include such other special mathematical expressions used or created to account for border effects and effects at the lateral periphery and at the furthest distance where $R_A$ may be reliably determined by application of the teaching of this disclosure.

If perfectly columnated light is assumed, the value of $R_A$ at the desired point will be the same as the reference $R_A$ value. In practice, all sign 190 sheeting materials will have some beam divergence for reflected light. This beam divergence information can be used to adjust the computed $R_A$ value up (or down) from the reference $R_A$ value for discrete locations closer to (or farther from) the object's face surface 130.

While knowing the normal vector 180 to a sign 190 face is not required, there are some advantages for planning and maintenance purposes that make the information useful. Several ways to compute the normal vector 180 for a sign 190 exist. First of all, the "assumption" method requires that the normal vector 180 from the surface of the sign 190 is assumed to be parallel to the capture vehicle pathway 410 at the nearest location of the capture vehicle pathway 410 to the sign 190. Second, a scanning laser operating in conjunction with an optical sensor and having a common field of view may be used to more precisely resolve the normal vector 180 from the object's face surface 130. Third, stereoscopic cameras 360 may be employed in a useful, albeit very imprecise manner of determining the normal vector 180. Fourth, the assumption method and stereo imaging method may be combined whereby the normal vector 180 is assumed to lie parallel to the vehicle pathway 410 unless the stereo imaging output renders the assumption false.

Of the methods listed above, the highest precision measuring systems for determining the normal vector 180 consists of a scanned laser and associated optical sensor. This combination yields relative distance measurements between the capture vehicle 225 and the object's face surface 130 that are more precise than optical measurements with cameras. A laser scanner attached to the capture vehicle 225 and directed toward a roadside scene populated with retroreflective signs 130 generates a series of reflection points to the optical sensor that appear as a horizontal segment of points. The optical sensor must be fast enough (i.e., have adequate data acquisition rates) to capture at least several individual discrete measurements across the object's face surface 130 (or of any other reflective asset). In general, two types of laser scanners are suitable to be utilized according to the present invention; namely, single-axis scanners and dual-axis scanners. A preferred sensor is of the type set forth in the proposal entitled, "Holometrics 3-D Vision Technology," as referenced in the previously identified provisional patent application.

Since most all types of roadside signs 190 to be measured are disposed at various elevations relative to the highway 150 and the capture vehicle 225, a single-axis laser scanner cannot be mounted such that the scanning laser beam covers only a single elevation or constant height relative to the highway 150 and the capture vehicle 225. Rather, the inventors hereof suggest that use of a single-axis type laser scanner must either be mounted high on the capture vehicle 225 with a downward facing trajectory, or be mounted low on the capture vehicle 225 with an upward facing scanning trajectory. These two mounting schemes for a single-axis laser scanner help ensure the lateral scan will intersect with virtually every object face surface 130 of all signs 190 or other objects of interest 460 present in a roadside scene regardless of the elevation or height or such signs relative to the roadway or to the moving platform.

Dual-axis laser scanners 335 circumvent the varying sign height problem inherently encountered if a single-axis laser scanner is employed as the source of integrated energy when practicing the teaching of the present invention. A dual-axis laser scanner 335 operates by continuously moving the scanning beam scan up and down at a relatively slow rate while sweeping the laser beam laterally from side to side across the field of view at a relatively more rapid rate.

In order to obtain the normal vector 180 for a sign 190 as taught hereunder, only a select horizontal series of discrete locations across the object's face surface 130 needs to be sensed by the high-speed optical sensor. For each point in the horizontal series of discrete locations recorded for a given sign 190 due to the incident radiation provided by the scanning laser, as sensed by the high speed optical sensor, the precise direction of the incident laser is recorded, thus allowing both distance and direction of the measured point to be determined.

Either of the scanning methods produces a massive number of sensed discrete locations representing discrete reflections of the incident laser radiation and each must be processed in order to correlate each of the sensed discrete locations with the object's face surface 130. Once the lateral series of discrete locations for a sign 190 is determined, simple triangulation methods are used to combine: (i) the vehicle location, (ii) vehicle heading vector, and (iii) scanned sign point to ultimately determine the normal vector 180 for the object's face surface 130.

As stated earlier, knowing the sign's 190 normal vector 180 can expand the utilization of the present invention. The retroreflective properties of sign 190 sheeting materials are typically symmetrical about the vertical axis of the object's face surface 130. Because of this symmetry, $R_A$ values (either computed or extrapolated/interpolated values) will be identical for rays that are symmetrical about the vertical axis.

FIG. 10 shows how the sign's 190 normal vector 180 can be used to extrapolate more $R_A$ points. The $R_A$ value for Point B is the same as the $R_A$ value for Point A since their angle relative to the normal vector 180 is the same and since their distance from the sign 190 is the same. If Point B has the same relative angle (from the sign's 190 normal vector 180) as Point A, but lies closer to (or farther from) the object's face surface 130, the sign 190 material's beam divergence profile can be used to adjust the $R_A$ value for Point B up (or down) from the value obtained for Point A.

The image capture system 250 and light intensity measurement system 230 are preferably free running, with measurements being made periodically during capture vehicle 225 operation. There is no requirement that these two systems be synchronized. In fact, these systems could operate in completely different capture vehicles 225, if necessary. When both systems are contained within the same capture vehicle 225, the only constraint for simultaneous operation is placed on the image capture system 250. Because of the intensity of the high output light source 270 in the light intensity measurement system 230, it is preferred that the image capture system 250 not capture frames at the same instant that the high output light source 270 is triggered. If images are actually captured while the high output light source 270 is triggered, their positional results would still be valid, but the colors displayed would be inaccurate because of the high output light being directed toward the (typically lower-thresholded) stereoscopic cameras 360.

One skilled in the art could completely eliminate any need for the image capture system 250 to know the firing events of the light intensity measurement system 230 by choosing sampling rates for the two systems that do not share any harmonic frequencies. On the rare occasions when the image capture system 250 captures images while the high output light source 270 is energized (or flashed), the skilled implementer could use time stamps to determine when this system simultaneity occurred and discard the imaging frames.

Figures 1, 14B:
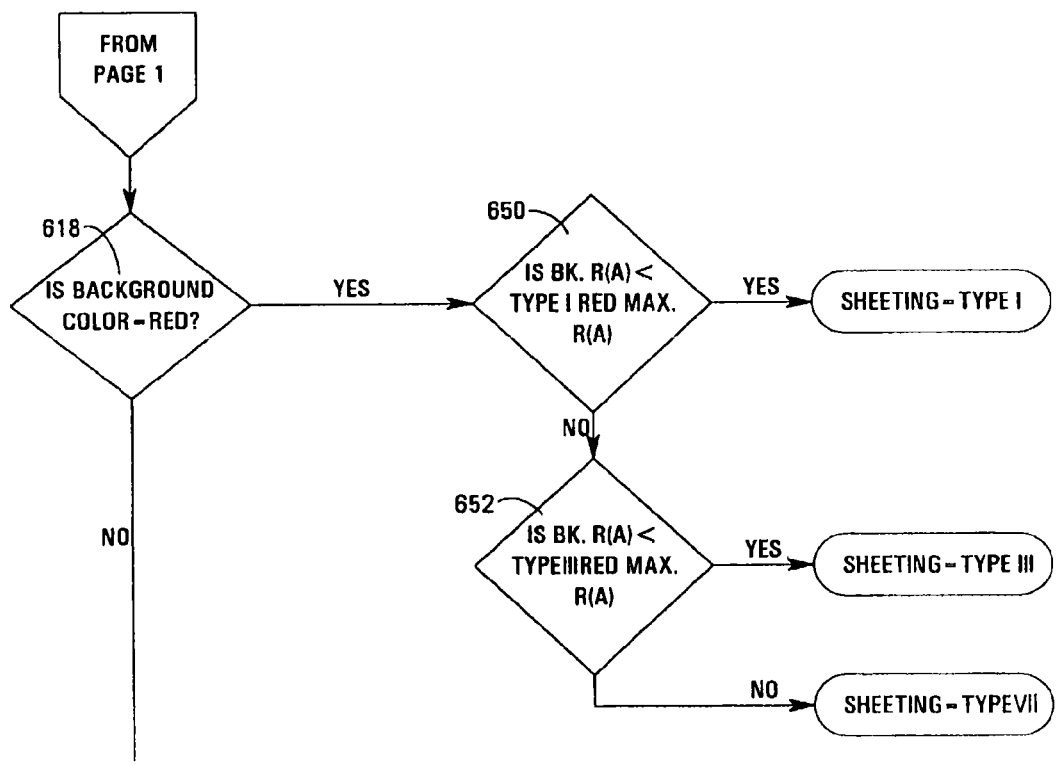
Figures 2, 14B:
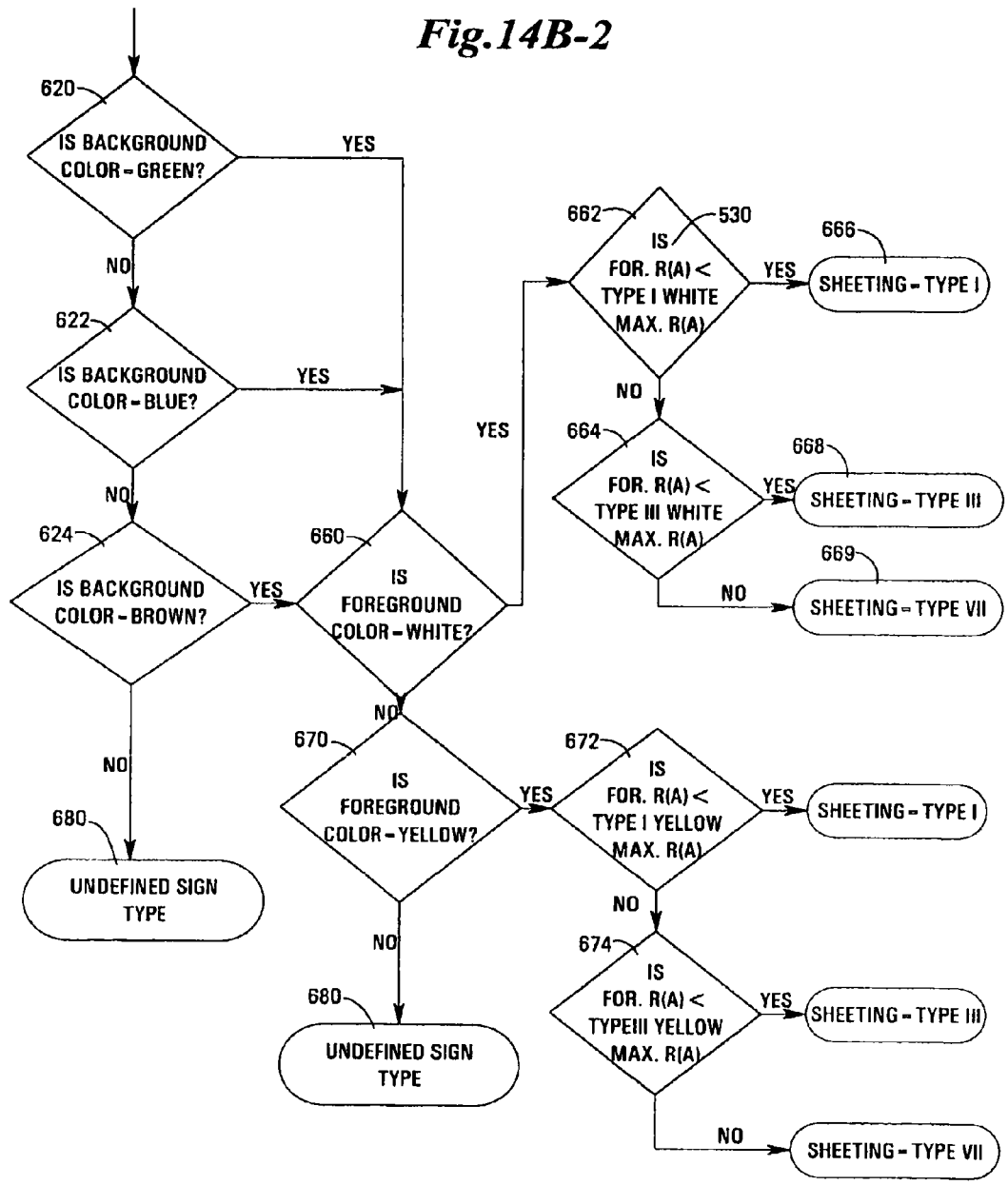

Referring now to FIGS. 14A and 14B, a preferred embodiment of the flowchart for the sign sheeting threshold algorithm will be described. In the preferred embodiment, certain assumptions are made that simplify the threshold algorithm process. It will be understood that additional assumptions could be made to further simplify the process, or that the process could be further expanded to allow certain of the assumptions to be avoided. In the preferred embodiment, it is assumed that each road sign 30 has only two colors of reflective sheeting and that the sheeting type is the same for both the background sheeting color 505 and the foreground sheeting color 506. It is also assumed that the retroreflectivity for both the background $R_A$ 520 and the foreground $R_A$ 530 are non-zero values. As previously described, the algorithm assumes that prefiltering has eliminated retroreflectivity values for road signs 30 that demonstrate some type of gross failure of the sheeting material, such as delamination, excessive surface wear, extreme color fade, vapor fade, graffiti, or excessive dirt or other obstructions that would prevent an accurate determination of the retroreflectivity value. Such filtering is preferably accomplished by image analysis of the color images using any number of known image analysis techniques for characterizing anomalies in images.

The sign sheeting threshold algorithm process is initiated at step 600. At steps 610-624, the background sheeting color 505 is compared to a series of known sign sheeting colors. If the background color is yellow-green as determined at step 610, then the sign sheeting type is classified as Type VII as step 628. If the background color is white as determined at step 612, then the background $R_A$ 520 is compared to the maximum retroreflectivity values for different sheeting types at steps 630, 632. If the background $R_A$ 520 is less than the maximum white retroreflectivity value for sheeting Type I as determined at step 630, then the sign sheeting type is classified as Type I at step 634. Otherwise, if the background $R_A$ 520 is less than the maximum white retroreflectivity value for sheeting Type III as determined at step 632, then the sign sheeting type is classified as Type III at step 636. If neither steps 630 or 632 are satisfied, then the sign sheeting type is classified as Type VII at step 638. A similar process is repeated for colors yellow at step 614 and steps 640, 642, orange at step 616 and steps 644, 646, red at step 618 and steps 650, 652.

If the background color is either green, blue or brown, as determined at steps 620, 622 and 624, then a second determination is made at step 660 whether the foreground color 506 is white and at step 670 whether the foreground color is yellow. If step 660 is satisfied, then the foreground $R_A$ 520 is compared to the maximum retroreflectivity values for different sheeting types at steps 662, 664. If the foreground $R_A$ 530 is less than the maximum white retroreflectivity value for sheeting Type I as determined at step 662, then the sign sheeting type is classified as Type I at step 666. Otherwise, if the foreground $R_A$ 530 is less than the maximum white retroreflectivity value for sheeting Type III as determined at step 664, then the sign sheeting type is classified as Type III at step 668. If neither steps 662 or 664 are satisfied, then the sign sheeting type is classified as Type VII at step 669. A similar process is repeated for the yellow foreground color at steps 672 and 674.

In the event that the background color 505 was not identified in steps 610-624 or the foreground color 506 was not identified in steps 660, 670, the sign sheeting type is considered undetermined at step 680. It will be understood that various options can be undertaken at step 680, including obtaining another color image and set of retroreflectivity values for the given road sign either with or without additional filtering or preprocessing of the raw data, marking the image and data for further review by an operator, discarding the information and marking the road sign as needing manual investigation, marking the road sign as needing replacement, or any combination of these or other operations.

Although the preferred embodiment of the threshold algorithm has been described with respect to the use of maximum retroreflectivity values, it will be understood that the threshold algorithm could utilize either minimum or maximum retroreflectivity values. Similarly, the combinations and orders of comparison of the colors and foreground or background colors may be altered and additional comparisons may be made to accommodate additional sheeting types that may be developed. Preferably, the colors 505 and 506 are determined based on CIELUV color values as evaluated by the image capture system 250. Alternatively, other equivalent color value systems such as RGB could be used for the color values. Preferably, the color values for the comparisons are a range of values specified by the manufacturer of the sheeting material. Alternatively, the color values for the comparison can be ranges of values empirically established.

The invention claimed is:

1. An automated system that detects and determines reflective surfaces of interest in a scene of non-retroreflective surfaces along a roadway that is being traversed by a vehicle, the automated system comprising:
   an image capture system that captures images within a field of view along the roadway;
   an active light sensor including:
      a light source that illuminates an area along the roadway; and
      a light sensor that measures light intensity values within at least a portion of the area illuminated by the light source; and
   a computer processing system operably connected to the image capture system, and the active light sensor and configured to detect objects of interest within the field of view and for each object of interest:
      determine whether the object of interest includes a reflective surface based on the light intensity values;
      determine whether the reflective surface is a road marker based on an assessment of the reflective surface; and
      determine a location of the road marker.

2. The automated system of claim 1, wherein the road marker is an object of interest selected from the set consisting of a road sign or a pavement marker.

3. The automated system of claim 1, wherein the computer processing system is configured to operate in a mode selected from post-processing or on-the-fly.

4. The automated system of claim 1, wherein the light source is selected from the set consisting of a laser scanning device, a strobe light, or a vehicle headlight lamp.

5. The automated system of claim 1, wherein the computer processing system is configured to determine the location of the road marker using the light intensity values for the reflective surface by using a location and heading of the active sensor and a location of the object of interest to determine a light vector emanating from the light source responsible for one of the light intensity values and comparing the light vector to one of a plurality of predetermined vectors based on a light source angle characterization.

6. The automated system of claim 5, wherein the light source angle characterization is a look-up-table that relates an angular displacement from a normal vector for the light source to a light intensity for the light vector associated with the reflective surface.

7. The automated system of claim 5, further comprising a global positioning satellite (GPS) unit that determines a location of the vehicle operably coupled to the computer processing system, wherein the location of the vehicle is used in determining the location of the road marker.

8. The automated system of claim 1, wherein the computer processing system is further configured to associate at least one color with the reflective characteristic of the road marker to confirm the assessment that the reflective surface is a road marker, wherein the at least one color is selected from a set of colors consisting of yellow, green, red and white.

9. An automated system for assessing reflective surfaces disposed along a roadway comprising:
   an active light sensor that is traversed along a roadway that includes at least one reflective surface on a road marker, the road marker having a reflective characteristic, the active light sensor including:
      a light source to illuminate an area that includes the at least one reflective surface; and
      a light sensor that measures a plurality of light intensity values within a field of view which includes at least a portion of the area illuminated by the light source; and
   a computer processing system operably connected to the active light sensor and configured to detect objects of interest within the field of view and for each object of interest:
      determine whether the object of interest includes at least one light intensity value associated with a reflective surface of a road marker in the field of view; and
      analyze the at least one light intensity value to determine an assessment of a discrete location of the road marker within the field of view.

10. The automated system of claim 9, wherein the road marker is selected from a set consisting of pavement markings and road signs.

11. The automated system of claim 9, wherein the computer processing system is configured to operate in a mode selected from post-processing or on-the-fly.

12. The automated system of claim 9, wherein the light source is selected from the set consisting of a laser scanning device, a strobe light, or a vehicle headlight lamp.

13. The automated system of claim 9, wherein the computer processing system is further configured to associate at least one color with the reflective characteristic of the road marker to confirm the assessment that what is positioned at the discrete location within the field of view is a road marker, wherein the at least one color is selected from a set of colors consisting of yellow, green, red and white.

14. The automated system of claim 9, wherein the computer processing system is further configured to determine an entrance angle and an observation angle of the road marker as part of the assessment of the discrete location of the road marker within the field of view.

15. The automated system of claim 9, wherein the computer processing system is further configured to determine exemplary angular displacements of incident light for each light intensity measurement from a reference position relative to the field of view as part of the assessment of the discrete location of the road marker within the field of view.

16. The automated system of claim 15, wherein each of the exemplary angular displacements of incident light comprises an observation angle corresponding to one of a plurality of distances of the light source from the road marker.

17. An automated method for assessing reflective surfaces disposed along a roadway comprising:
    activating a light source as the light source is traversed along a roadway to illuminate an area that includes at least one reflective surface on a road marker, the road marker having a reflective characteristic;
    determining a plurality of light intensity values with at least one intensity sensor directed to cover a field of view which includes at least a portion of the area illuminated by the light source; and
    using a computer processing system configured to:
        identify at least one light intensity value of the plurality of light intensity values associated with one of the at least one reflective surface of the road marker in the field of view; and
        analyze the at least one light intensity value of the plurality of light intensity values to determine an assessment of a discrete location of the road marker within the field of view.

18. The automated method of claim 17, wherein the computer processing system is further configured to associate at least one color with the reflective characteristic of the road marker to confirm the road marker at the discrete location within the field of view, wherein the at least one color is selected from a set of colors consisting of yellow, green, red and white.

19. The automated method of claim 17, further wherein the computer processing system is further configured to determine a lateral distance between the light source and the illuminated portion of the reflective road marker.

20. The automated method of claim 17, wherein the computer processing system is further configured to determine an entrance angle and an observation angle of the road marker.

21. The automated method of claim 17, wherein the computer processing system is further configured to determine exemplary angular displacements of incident light for each light intensity measurement from a reference position relative to the field of view.

22. The automated method of claim 21, wherein each of the exemplary angular displacements of incident light comprises an observation angle corresponding to one of a plurality of distances of the light source from the road marker.

* * * * *

Disclaimer

9,671,328 B2 - James E. Retterath, Excelsior; Robert A. Laumeyer, Eden, both of MN (US). SYSTEMS AND ASSESSMENT OF REFLECTIVE OBJECTIVES ALONG A ROADWAY. Patent dated June 6, 2017. Disclaimer filed by the assignee, Mandi Communications, Inc.

I hereby disclaim the following complete Claims 17-22 of said patent.

*(Official Gazette, February 18, 2025)*